United States Patent [19]

Steffen et al.

[11] 4,270,547

[45] Jun. 2, 1981

[54] VITAL SIGNS MONITORING SYSTEM

[75] Inventors: Dale A. Steffen, Aurora; Ronald E. Sturm; George A. Rinard, both of Denver, all of Colo.

[73] Assignee: University Patents, Inc., Norwalk, Conn.

[21] Appl. No.: 948,139

[22] Filed: Oct. 3, 1978

[51] Int. Cl.³ .............................................. A61B 5/02
[52] U.S. Cl. .................................. 128/671; 128/706; 128/723; 128/736; 364/415
[58] Field of Search ............................... 128/670–671, 128/688–690, 706, 709–710; 364/415–417; 340/784

[56] References Cited

U.S. PATENT DOCUMENTS

| 3,807,388 | 4/1974 | Orr et al. | 128/690 |
|---|---|---|---|
| 3,996,928 | 12/1976 | Marx | 128/671 |
| 4,053,951 | 10/1977 | Hudspeth et al. | 128/670 |
| 4,108,166 | 8/1978 | Schmid | 128/710 |
| 4,129,125 | 12/1978 | Lester et al. | 128/671 |

OTHER PUBLICATIONS

Ko, W. H. et al., "Microelectronics and Miniaturization," Ch. 73 in *Medical Engineering*, Yearbook Publishers, Chicago 1974, pp. 966–973.
Osborn, J. J. et al., "Measurement & Monitoring of Acutely Ill, Patients by Dig-Computer," *Surgery*, Dec. 1968, pp. 1057–1070.
Sheppard, L. C. et al., "Surgical IC Automation," *JAAMI*, Feb. 1972, pp. 74–78.

*Primary Examiner*—Robert W. Michell
*Assistant Examiner*—Francis J. Jaworski
*Attorney, Agent, or Firm*—O'Rourke & Harris

[57] ABSTRACT

A system is disclosed for monitoring vital physiological signs. Each of the system components utilizes a single hybrid circuit with each component having high accuracy without the necessity of repeated calibration. The system also has low power requirements, provides a digital display, and is of sufficiently small size to be incorporated into a hand-carried case for portable use. Components of the system may also provide independent outputs making the component useful, of itself, for monitoring one or more vital signs. The overall system preferably includes an ECG amplifier and cardiotachometer signal conditioner unit, an impedance pneumograph and respiration rate signal conditioner unit, a heart/breath rate processor unit, a temperature monitoring unit, a selector switch, a clock unit, and an LCD driver unit and associated LCDs, with the system being capable of being expanded as needed or desired, such as, for example, by addition of a systolic/diastolic blood pressure unit.

37 Claims, 14 Drawing Figures

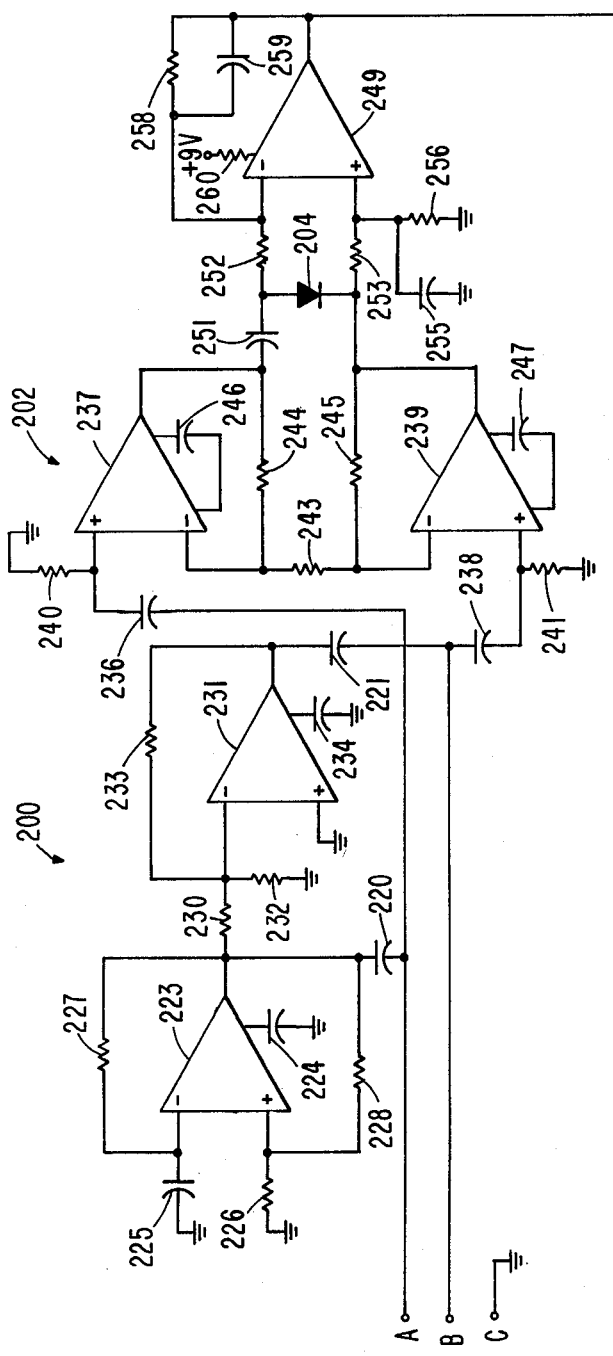
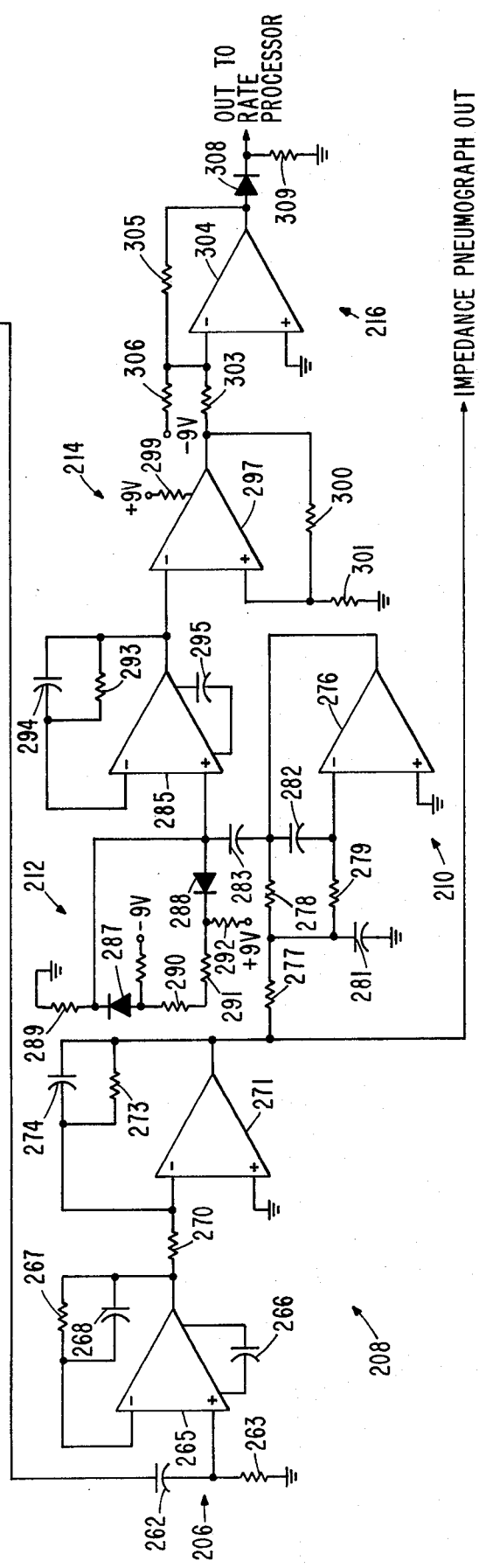
FIG. 4

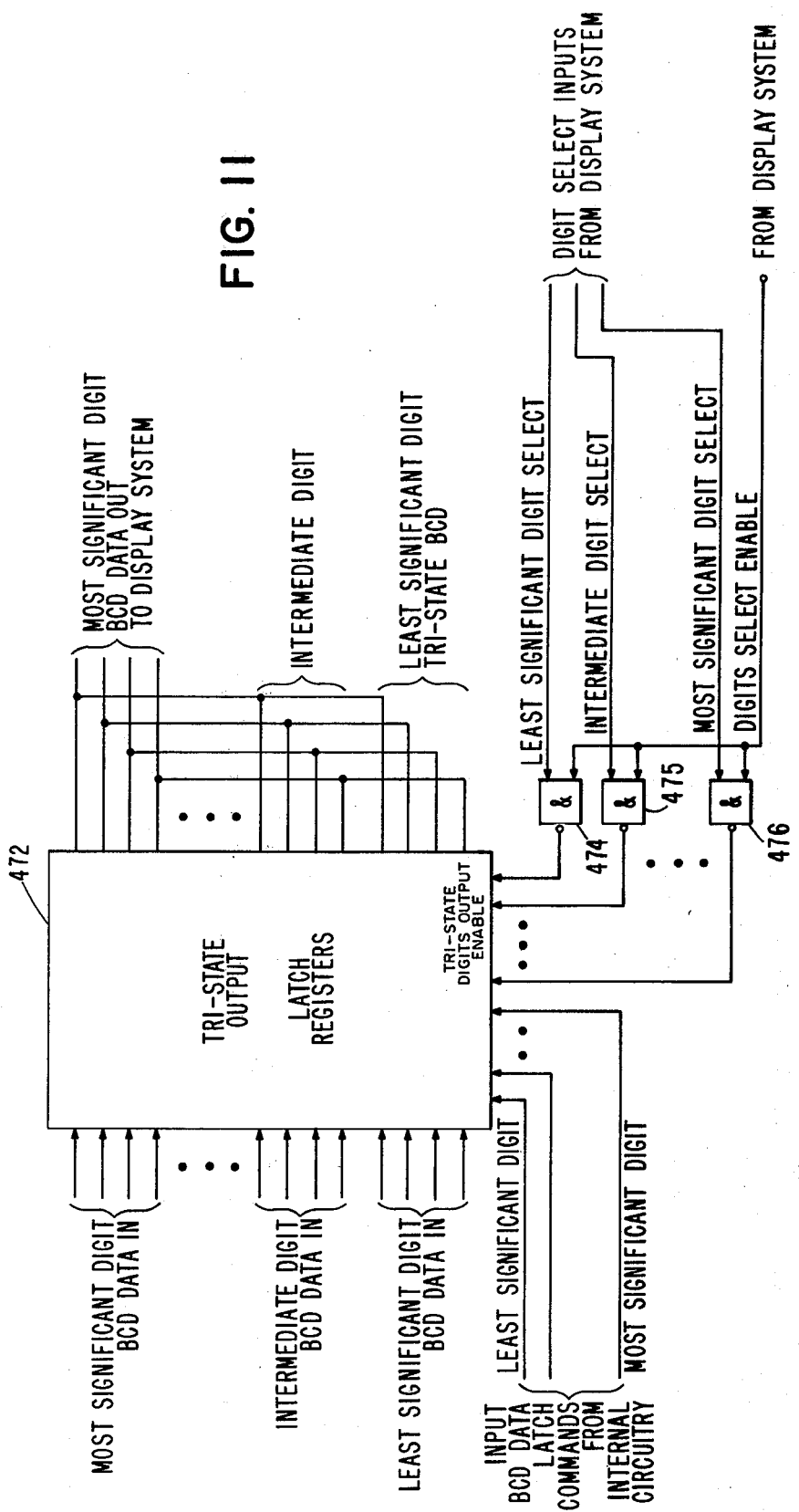

VITAL SIGNS MONITORING SYSTEM

GOVERNMENT RIGHTS

The invention described herein was made in the performance of work under NASA Contract No. NAS9-15206 and is subject to the provisions of Section 305 of the National Aeronautics and Space Act of 1958 (72 Stat. 435; 42 U.S.C. 2457).

FIELD OF THE INVENTION

This invention relates to a monitoring system and, more particularly, relates to a system having electronic components for monitoring vital physiological signs.

BACKGROUND OF THE INVENTION

It is often times desirable, and in some cases necessary, that the vital physiological signs of a patient be determined and monitored. The determinations and monitoring of various vital signs has long been carried out by heretofore existing equipment.

Various attempts have also heretofore been suggested and/or utilized to develop devices, including electronic devices, wherein a plurality of physical data, i.e., vital signs data, could be determined and displayed by the unit. Included in such suggested circuits is a unit that includes an electric thermometer, an ECG preamplifier, a heart beat detector, a heart rate processor, a pneumograph and a respiration rate processor. While this suggested art could determined and monitor a plurality of vital signs, a need still existed for an improved unit, as well as improved components for such a unit. By way of example, needed improvements include development of an electronic thermometer that does not require potentiometers for calibration or the use of circuit elements such as capacitors that are too large in value to be incorporated into a hybrid package, development of an ECG preamplifier that does not require discreet components that are not suitable for the space limitations that are imposed by small hybrid packaging, and development of a heart beat detector, heart rate processor, impedance pneumograph and respiration rate processor that do not require circuit elements such as potentiometers that must be mounted external of a hybrid package.

In general, existing vital signs monitoring devices have not been found to fully acceptable, at least for some purposes, due to high power requirements, unsuitability for hybridizing, utilization of low impedance levels, utilization of too many required calibration adjustments, lack of flexibility and/or use of components of larger dimensions than are acceptable for miniaturized packaging.

SUMMARY OF THE INVENTION

This invention provides an improved system for monitoring vital physiological signs that is stable and reliable. The system includes a plurality of improved units each of which includes components of small size and suitable for hybridizing, with each of the units having low power requirements and high impedance levels. The units of the system provide outputs suitable for an LCD digital display, and one or more vital signs can also be coupled from units of the system.

It is therefore an object of this invention to provide an improved system for monitoring vital physiological signs.

It is another object of this invention to provide an improved system for monitoring vital physiological signs having improved units therein.

It is still another object of this invention to provide an improved system for monitoring vital physiological signs that is stable and reliable.

It is still another object of this invention to provide an improved system for monitoring vital physiological signs that is miniaturized.

It is yet another object of this invention to provide an improved system for monitoring vital physiological signs each unit of which is hybridized into a single circuit.

It is yet another object of this invention to provide an improved system for monitoring vital physiological signs that has low power requirements and has high impedance levels.

It is still another object of this invention to provide an improved system for monitoring vital physiological signs that provides an LCD digital output display capable of displaying each vital sign monitored by the system.

It is yet another object of this invention to provide improved units for developing, processing and/or displaying vital physiological signs.

With these and other objects in view, which will become apparent to one skilled in the art as the description proceeds, this invention resides in the novel construction, combination, and arrangement of parts substantially as hereinafter described, and more particularly defined by the appended claims, it being understood that such changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which:

FIG. 4 is schematic diagram of the impedance pneumograph and respiration rate signal conditioner unit as shown in FIG. 2;

FIG. 11 is a schematic and block diagram showing generally the data output circuitry of the vital signs processors included in the system;

DESCRIPTION OF THE INVENTION

The vital signs monitoring system 17 of this invention provides a system which allows measuring and display, by electronic means, of vital signs such as body temperature, ECG, pulse rate, breath rate, and, optionally, blood pressure. The system is miniaturized and portable, with the circuitry of each unit being a single hybrid circuit. Hence, the system is well suited for utilization in a variety of different situations such as, for example, in remote areas or in tight spaces.

The term hybrid as used herein refers to a number of different means of fabricating an electronic circuit. Mostly these are packaging techniques for assembling miniature circuits. Specifically, these circuits are assembled using a combination of thin film and semi-conductor techniques and the hybrid circuit takes advantage of the best parts of the two techniques. The electronic components are assembled as unpackaged devices and the entire circuit is then enclosed in a single package. This greatly reduces the physical size of the circuit compared with conventional printed circuit board techniques. At least a portion of the circuits as disclosed herein could also be constructed utilizing semi-conductor technology alone, however, if desired.

Figure 1:
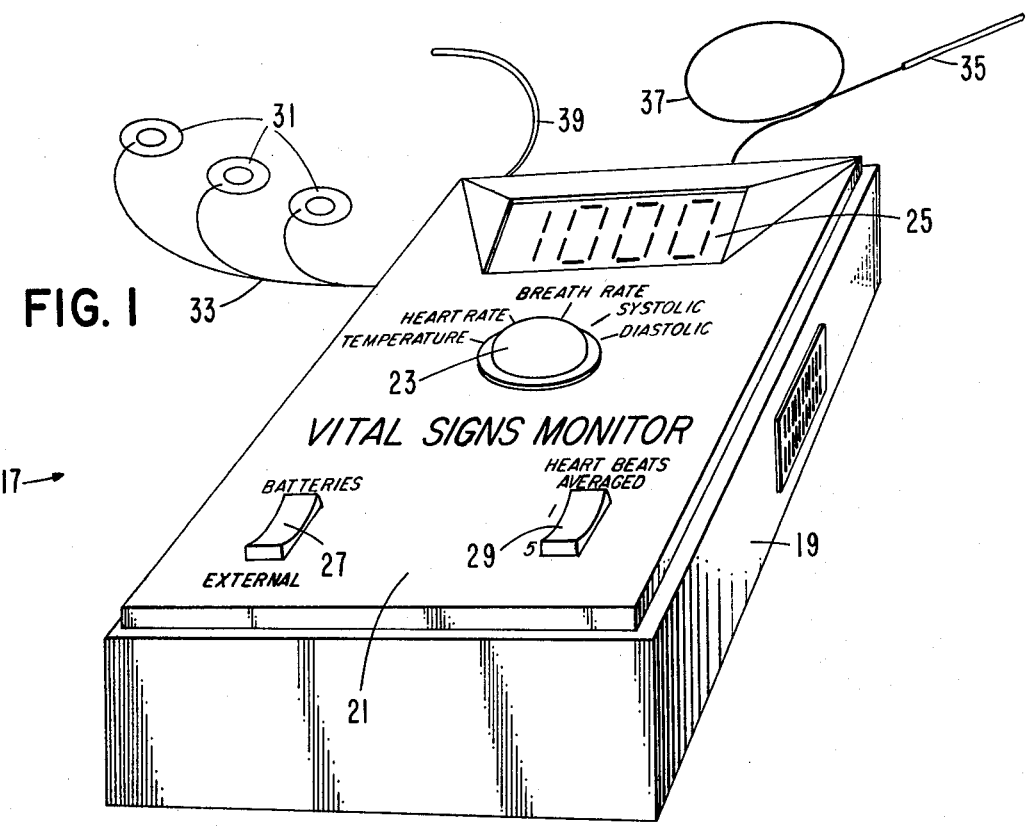
FIG. 1 is a perspective view of the vital signs monitoring system of this invention.

A first consideration, whenever a hybrid circuit is designed, is to reduce power dissipation and physical size as much as possible within reason. As shown in FIG. 1, the entire system 17 may be encased within a housing, or case, 19 of small dimensions (about 25 cm × 40 cm × 10 cm, for example) with the top 21 of the housing having a selector switch 23 thereat for selecting the particular vital sign then to be measured and displayed at digital display 25.

As also shown in FIG. 1, a switch 27 is provided to select battery or external power (the batteries when utilized are small batteries that are included within case 19), and a switch 29 is provided to select heart beats determined on a per-beat basis or on an average of 5 beats.

Patient engageable electrodes 31, external of housing 19, are coupled through leads 33 to the system circuitry (within housing 19), while temperature probe 35, also external to housing 19, is coupled to the system circuitry within the housing through leads 37, and leads 39 extending from housing 19 are the power leads for connecting the system to a conventional external power supply.

Figure 2:
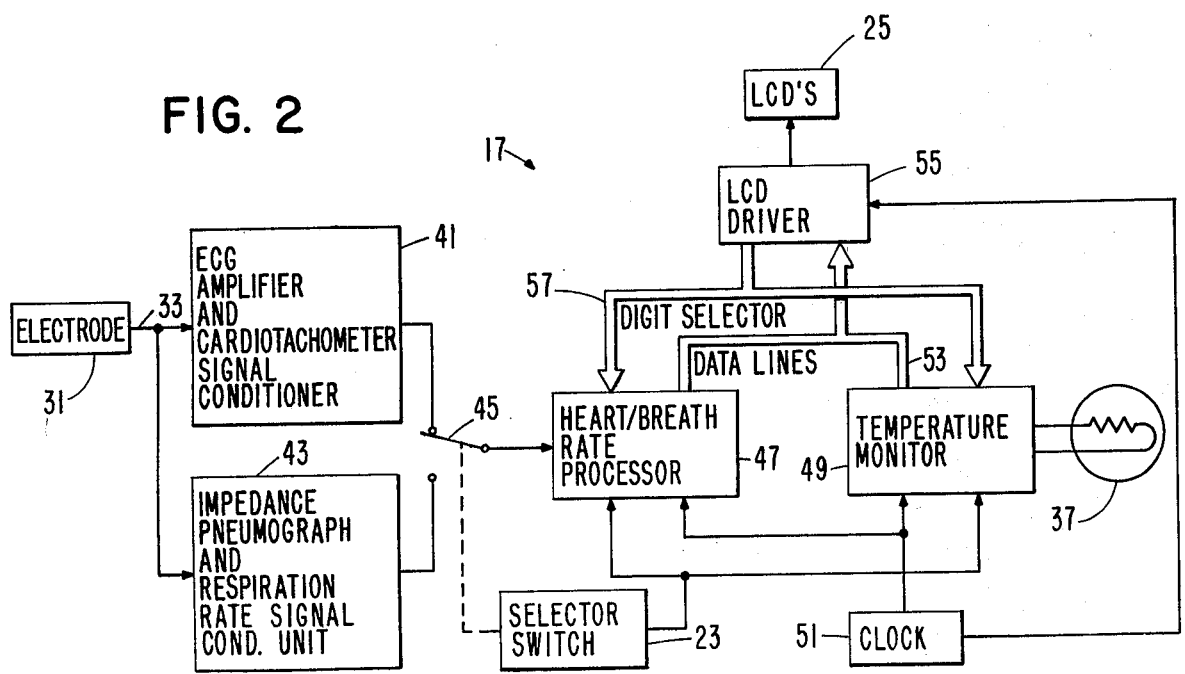
FIG. 2 is a block diagram of the vital signs monitoring system of this invention.

As shown in FIG. 2, the vital signs monitoring system of this invention includes an interconnected series of units, including ECG amplifier and cardiotachometer signal conditioner unit 41 and impedance pneumograph and respiration rate signal conditioner unit 43, both of which are connected to electrodes 31 through leads 33 (a plurality of electrodes are utilized each of which has a separate lead to units 41 and 43 as brought out more fully hereinafter). As is well known, electrodes 31 are placed in contact with a patient in order to sense vital signs, such as heart beat, pulse rate and breath rate.

Units 41 and 43 are connected through switch 45 (controlled by selector switch 23) to heart/breath rate processing unit 47. A temperature monitoring and processing unit 49 is also provided with units 47 and 49 having a clock circuit 51 connected therewith for timing purposes.

Four data lines (indicated generally by the numeral 53 in FIG. 2) are connected from heart/breath rate processing unit 47 and temperature monitoring unit 49 to LCD driver unit 55, with unit 55 providing digit select information back to units 47 and 49 on digit selector lines (generally designated in FIG. 2 by the numeral 57). LCD driver unit 55 also receives an input from clock unit 51 for timing purposes and drives LCDs 25 to visually display all monitored vital signs in digital form.

Figure 3:
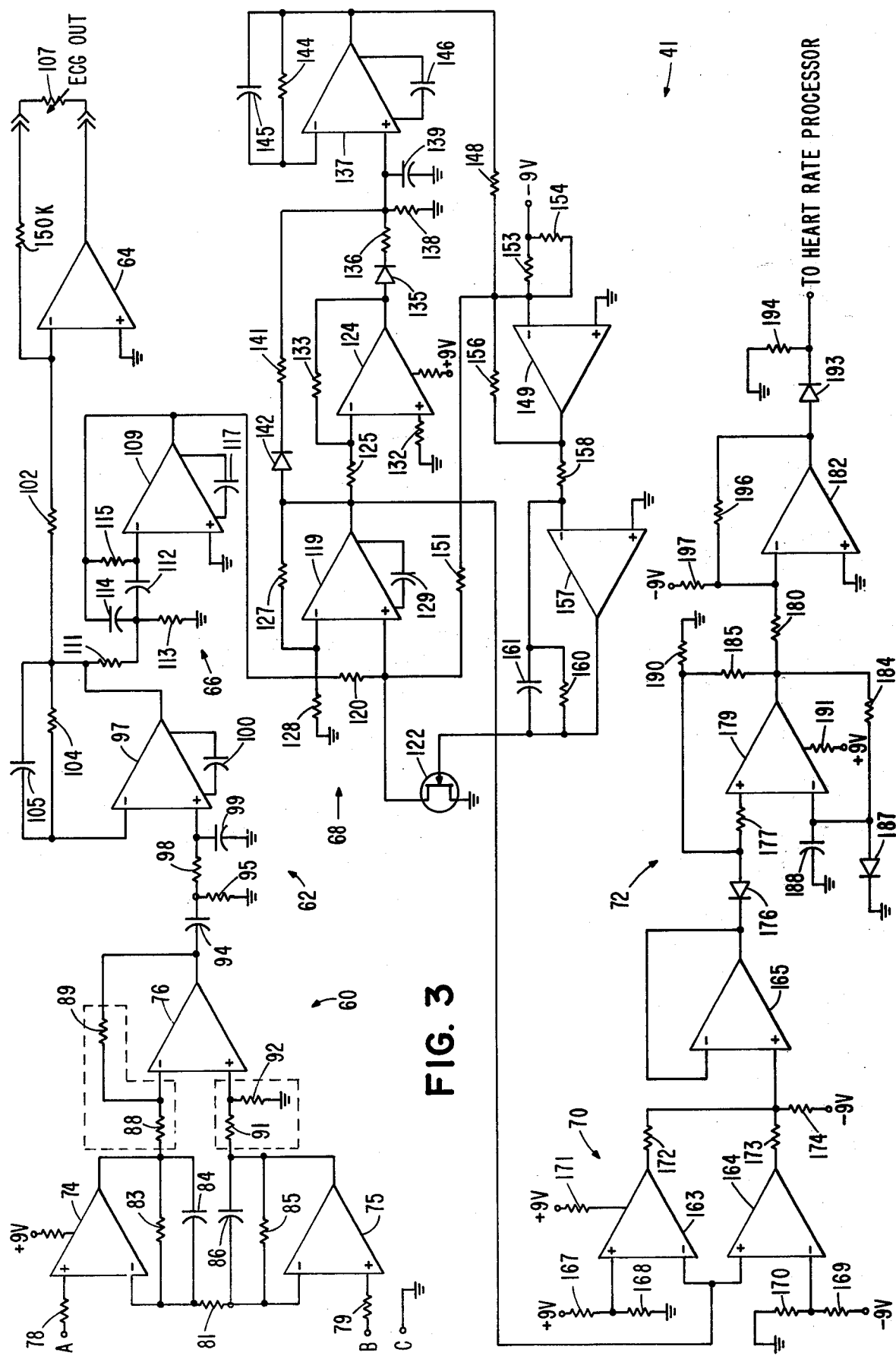
FIG. 3 is a schematic diagram of the ECG amplifier and cardiotachometer signal conditioner unit as shown in FIG. 2.

ECG amplifier and cardiotachometer signal conditioner unit 41 is shown in detail in FIG. 3. This unit requires low power and is miniaturized in a single hybrid package as are all of the other units included in this system. In addition, unit 41 provides a high common mode rejection ECG amplifier and produces a pulse suitable for digital circuits that can be reliably used to determine heart rate.

Prior known devices of this type commonly utilized either discreet component circuitry or operational amplifiers and also used full wave rectifiers to alleviate the effect of reverse polarity. Included in the primary limitations of such prior known devices have been component large dimensions, high power consumption, and use of many components that had to be adjusted in common mode rejection and pulse height detector units.

A fixed gain cardiotachometer signal conditioner, for example, requires the operator to adjust a threshold level for pulse discrimination at a specific amplitude. When this amplitude then changes, the threshold must be manually readjusted to obtain the pulse. Some prior known circuits have used automatic gain to eliminate this problem, but there circuits have normally required adjustment of the automatic gain level, unlike unit 41, where no such adjustment is required.

Unit 41 provides an ECG amplifier which includes pulse forming circuitry suitable for input into a cardiotachometer. This pulse forming circuitry utilizes an automatic gain circuit so that a pulse will be formed over a wide range of amplitude of input signal. While unit 41 is particularly useful in the vital signs system to provide a digital display, an output is also provided from this unit to enable the unit to be used separately with other ECG displays (strip charts or oscilloscopes, for example) or as an input to a cardiotachometer circuit.

As shown in FIG. 3, unit 41 receives the heart signal from three electrodes 31 (designated as inputs A, B, and C in FIG. 3 with input C being the common, or reference, electrode). The heart signal is first amplified by balanced differential amplifier 60 having very high input impedance and large common mode rejection. The heart signal is then fed to a bandpass filter 62 to suppress unwanted noise and interference. An amplifier 64 with adjustable gain provides the low output impedance necessary to form the ECG output from the heart signal.

The filtered heart signal, after additional filtering at filter 66, is fed to a normalizing circuit 68 which standardizes the amplitude of the pulse regardless of polarity. A bipolar threshold circuit 70 is used to detect the time of occurrence of the QRS pulse. The threshold output pulse is then standardized in width and amplitude by circuitry 72 for use by the heart rate processor.

Balanced differential amplifier 60 consists of three operational amplifiers 74, 75, 76, contained on one chip as shown in FIG. 3. Electrodes 31 A and B are connected with the positive input of operational amplifiers 74 and 75, respectively, through resistors 78 and 79, respectively, while the negative inputs of amplifiers 74 and 75 are connected to one another through resistor 81, and the outputs of amplifiers 74 and 75 are fed back to the negative inputs through parallel connected resistor 83 and capacitor 84 (amplifier 74) and resistor 85 and capacitor 86 (amplifier 75). The output from amplifier 74 is coupled through resistor 88 to the negative input of operational amplifier 76 (which negative input also receives the signal fed back from the output through resistor 89), and the output from amplifier 75 is coupled through resistor 91 to the positive input of operational amplifier 76 (which input is also connected with ground through resistor 92).

The quiescent current can be made adjustable by selection of a set resistor and preferably is selected for approximately 15 microamps for each amplifier. This is possible since the bandwidth required is very modest which also ensures input impedance well above the required 40 megohms differential and common mode. Because the input circuit is identical for both differential and common mode signals, the amplifier is truly balanced. The input amplifier pair 74 and 75 also possesses the unique property that the gain for differential signals is +40 db, whereas common mode signals commonly receive only unity gain. Thus, the final amplifier 76 in this group of three, which is connected as a standard difference amplifier, need only contribute 50 db to the CMRR since the input amplifier pair 74 and 75 supplies 40 db of the required 90 db total.

The output from amplifier 76 is coupled to filter 62. At filter 62, capacitor 94 and resistor 95 determine the low frequency cutoff of 0.05 Hz for the heart signal. To ensure that capacitor 94 is of reasonable physical size, resistor 95 must be of very high resistance.

Operational amplifier 97 (positive input) is connected with the junction of capacitor 94 and resistor 95 through resistor 98 (with the positive input also having a bypass capacitor 99 to ground and the amplifier also having an additional circuitry capacitor 100). Amplifier 97 must be selected for low offset current as well as low quiescent power dissipation. The selected type (MLM108) exhibits input offset of 0.4 nanoamps maximum, and power supply current of only 300 microamps typical. Output offset voltage at amplifier 97 will thus be $0.4 \times 10^{-9} \times 6.8 \times 10^6 = 2.7$ millivolts maximum.

The output from amplifier 97 is coupled through resistor 102 to the negative input of ECG output amplifier 64. This output is also fed back to the negative input of amplifier 97 through parallel connected resistor 104 and capacitor 105.

ECG output amplifier 64 has a gain adjustable from 6.25 to 48. At maximum gain, the d.c. offset at the ECG output (shown connectable with a 1 M variable resistor 107) will not exceed $2.7 \times 10^{-3} \times 48 = 0.125$ volts.

The output from amplifier 97 is also coupled to filter 66 which includes amplifier 109 and associated circuitry which together constitute a high impedance active bandpass filter with low output impedance. As shown, the output from amplifier 97 is coupled through resistor 111 and capacitor 112 to the negative input of amplifier 109, with the junction of resistor 111 and capacitor 112 having a resistor 113 to ground. The output of amplifier 109 is fed back to the opposite sides of capacitor 112 through capacitor 114 and resistor 115, and amplifier 109 has an additional circuit capacitor 117 connected therewith. The center frequency of filter 66 is 17 Hz with Q=3. This filter prevents cardiotachometer triggering on abnormally large T waves.

The filtered ECG signal from amplifier 109 is normalized by circuitry 68. Circuitry 68 includes high gain amplifier 119 which receives the output signal from amplifier 109 at the positive input through resistor 120. The positive input of amplifier 119 is also connected to FET 122 with FET 122 becoming a variable shunt attenuator controlling the overall gain of the amplifier.

As shown in FIG. 3, the output of amplifier 119 is connected with the negative input of inverter 124 through resistor 125, and is fed back to the negative input through resistor 127. The negative input of amplifier 119 is also connected with ground through resistor 128, and amplifier 119 has an additional capacitor 129 in the circuit. Inverter 124 is connected to a +9 volt power source through resistor 131, has the positive input connected with ground through resistor 132, and has the output fed back to the negative input through resistor 133.

In addition, the output of inverter 124 is coupled to one side of diode 135, the other side of which is connected through resistor 136 to the positive input of voltage follower 137, with the junction of resistor 136 and the positive input of voltage follower 137 being connected with ground through parallel connected resistor 138 and capacitor 139. The junction of resistors 136 and 138 is connected through resistor 141 to one side of diode 142, the other side of which is connected to the output of amplifier 119. The output of voltage follower 127 is fed back to the negative input through parallel connected resistor 144 and capacitor 145, and voltage follower 137 also has an additional capacitor 146 in the circuit.

In this manner, the output of amplifier 119 and inverter 124 are full wave peak detected by diodes 135 and 142 and capacitor 139. The maximum peak amplitude, regardless of polarity, is therefore stored on capacitor 139 and transferred to the output of voltage follower 137.

The output from voltage follower 137 is coupled through resistor 148 to the negative input of summing amplifier 149, with the peak detector output being combined with a portion of the original filtered ECG signal (coupled through resistor 151) to linearize the FET voltage characteristics.

The negative input of summing amplifier 149 is also connected with a −9 volt power supply through parallel connected resistors 153 and 154, the latter of which is selected to get a d.c. operating voltage at the gate of FET 122 thereby calibrating the normalized output at the output of amplifier 119 at 2 volts peak.

The output of summing amplifier 149 is fed back to the negative input through resistor 156, and is also coupled to the negative input of inverter 157 through resistor 158. The output of inverter 157 is used to drive the gate of FET 122, and the output of inverter 157 is also fed back to the negative input through parallel connected resistor 160 and capacitor 161.

The filtered ECG signal output from amplifier 119 (see largest peak of which, as brought out hereinabove, will become 2 volts peak regardless of input amplitude over the specified range) is coupled to bipolar threshold circuit 70 which includes operational amplifiers 163, 164, and 165. The output from amplifier 119 is coupled to the negative input of amplifier 163 and to the positive input of amplifier 164. The positive input of amplifier 163 is connected to the junction of resistors 167 and 168 forming a voltage divider between a +9 volt power source and ground, while the negative input of amplifier 164 is connected to the junction of resistors 169 and 170 forming a voltage divider between a −9 volt power source and ground (amplifier 163 also is connected to the +9 volt power supply through resistor 171—a 10 M resistor). This biases amplifiers 163 and 164 at plus and minus 1.5 volts, respectively, so that the bipolar threshold circuit reacts whenever the normalized signal exceeds this value, either positive or negative.

The outputs from amplifiers 163 and 164 are connected to the positive input of amplifier 165 through resistors 172 and 173, respectively, with the positive input also being connected to a −9 volt power source through resistor 174.

The output from amplifier 165 is coupled to circuitry 72, and, more particularly, through diode 176 and resistor 177 to the positive input of amplifier 179. Amplifier 179 has its output coupled through resistor 180 to the negative input of amplifier 182, fed back through resistor 184 to the negative input, and fed back through resistor 185 to the junction of diode 176 and resistor 177. The negative input of amplifier 179 is connected with ground through diode 187 and capacitor 188, the junction of diode 176 and resistor 177 is connected with ground through resistor 190, and amplifier 179 is connected with a +9 volt power source through resistor 191.

The output from amplifier 182 is coupled through diode 193 to the output lead to heart/breath rate processor unit 47 (through switch 45 as shown in FIG. 2), which lead is connected with ground through resistor 194. The output from amplifier 182 is also fed back to the negative input through resistor 196, with the negative input also being connected to the −9 volt power source through resistor 197.

In a working embodiment of unit 41, the following ECG preamplifier specifications were utilized:

| Input Impedance | 40M Ωmin differential and each side of ground |
|---|---|
| DC Offset | Able to withstand ±0.05 VDC differentially input while operational |
| Input Circuit | True differential 0.5 μa max input lead current under any operating conditions. Compatible with 50 kHz ±5 kHz across input leads |
| Source Impedance | 1 to 100K ohms |
| Source Unbalance | 1 to 100K ohms in either input lead |
| Analog Output Level | ∓2.5 volts |
| Impedance | 200 Ωmax (resistive) |
| Frequency Response | ±0.5db from 0.14 Hz to 35 Hz −3db ±1db at 0.05 Hz and 100 Hz |
| Harmonic Distortion | Less than 1% |
| Recovery Time | 24 sec from 2 volt input pulse |
| Common Mode Rejection | 90 db min w/shorted input |
| Output Noise | 10 μv p-p referred to input |
| Gain Range | 600 to 4500 continuously variable |
| Stability | Able to tolerate ±1% power voltage step |
| Ripple | −80db at 100mv 8 to 15 kHz on power input |

No peripheral equipment other than power supplies and display are required for unit 41, and unit 41 supplies an ECG signal output and a pulse for input to the heart/breath rate processor unit 47.

By way of illustration, the following components may be utilized in unit 41:

Amplifiers: 64, 74, 75, 76, 124, 149, 157, 163, 164, 165, 179, and 182—L144/B; and 97, 109, 119 and 137—MLM108.

FET 122—2N4339.

Diodes: 135 and 142—FD300; and 176, 187 and 193—HPA2810.

Resistors: 78 and 79—100 k; 81—20 k; 83 and 85—1 M; 88, 89, 91 and 92—100 k; 95—6.8 M; 98—130 k; 102—24 k; 104—6.8 M; 107—1 M; 111—470 k; 113—240 k; 115—5.6 M; 120—11 k; 125 and 127—1 M; 128—10 k; 131—10 k; 132—510 k; 133—1 M; 136—20 k; 138—50 M; 141—20 k; 144—50 M; 148—1 M; 151—2 M; 153—4.3 M; 154—selectable (7.5 M-20 M); 156, 158, 160 and 167—1 M; 168—200 k; 169—1 M; 170—200 k; 172, 173 and 174—1 M; 177—100 k; 180—1 M; 184—5 M; 185—1 M; 190—200 k; 191—10 M; 194—1 M; 196—510 k; and 197—1 M.

Capacitors: 84 and 86—180 pf; 94—0.47 μf; 99—0.012 pf; 100—100 pf; 105—0.001 μf; 112 and 114—0.01 μf; 117—100 pf; 129—27 pf; 139—0.47 μf; 145—0.001 μf; 146—100 pf; 161—27 pf; and 188—0.12 μf.

Impedance pneumograph and respiration rate control conditioner unit 43 is also connected, as indicated in FIG. 2, to electrodes 31 through leads 33, and the unit is shown in greater detail in FIG. 4.

This unit is also a small size, low power unit that detects breathing via chest mounted ECG electrodes 31. An output pulse is provided that is suitable for digital circuit input so that respiration rate can be calculated and digitally displayed.

In this unit, the breath monitoring circuitry does not interfere with normal ECG monitoring. Also, this unit handles a problem that arises since the impedance of the chest as measured by the pneumograph can have a large change in its base value (due to respiration being at a very slow rate of six to twenty-four breaths per minute, a long time constant is required) which causes the pneumograph to be inoperative for up to a minute before the breath signal resumes.

Past techniques have utilized transformer coupling to the electrode leads and have also utilized long time constants to detect breath signals. In addition, large discreet component printed circuit board technology was used. Among the limitations of past technology is that due to the physical size of the transformers for transformer coupling and that due to potentiometer adjustments that were heretofore required for use.

An output respiration signal is produced in analog from as well as a pulse for use in the breath rate processor 47. Unit 43 is in hybrid form, and the circuit is suitable for operation independently from the other circuits in the vital signs system although it is particularly well adapted for use therewith.

Unit 43 measures the change in impedance at 50 kHz of the chest as it expands and contracts during the breathing cycle. The same electrodes 31 A, B, and C as used for the heart signal are simultaneously driven with balanced 50 kHz current by generating circuitry 200. The balanced voltage developed across the chest impedance is first amplified by amplifier circuitry 202 and then rectified by rectifier 204 since the breathing cycle acts as amplitude modulation for the 50 kHz signal. A simple bandpass filter 206 is used to remove undesirable noise which occurs beyond the required passband. After additional gain provided by amplifier circuitry 208, the breath signal has been formed into the impedance pneumograph signal.

The impedance pneumograph signal is also subjected to an additional low pass filter 210 followed by a balanced d.c. restorer 212. A threshold circuit 214 with hysteresis is followed by an output circuit 216 which standardizes the amplitude for use by the breath rate processor.

The impedance pneumograph depends upon the change in impedance across the chest as breathing takes place. It is necessary to provide balanced (with respect to the common electrode C) constant current at 50 kHz not exceeding 500 microamps peak. Another specification requires that the isolation at 0 to 100 Hz must exceed 10 megohms, but may be as low as 10 kilohms at 50 kHz. This unit utilizes capacitors 220 and 221 to supply balanced current to the patient, or subject, as shown in FIG. 4.

Since the chest impedance is very nearly resistive, the excitation circuit acts as a differentiator, which limits the excitation voltage waveshape that can be used. Ideally a squarewave of current would produce the largest rectified d.c. voltage across the chest resistance for a given peak current. The integral of a squarewave is a triangular wave which is the waveshape used in the circuit for unit 43.

As shown, a 50 kHz triangular wave generator (including amplifier 223) is utilized due to the slow rate limitation that is adjustable by capacitor 224.

Amplifier 223 has its negative input connected with ground through capacitor 225, its positive input connected with ground through resistor 226, and its output fed back to the negative and positive inputs through resistors 227 and 228, respectively. The output from amplifier 223 is also coupled through resistor 230 to the negative input of inverter 231, which negative input is connected with ground through resistor 232. The output of inverter 231 is fed back to the negative input through resistor 233 and inverter 231 has a capacitor 234 in the circuit (like that of amplifier 223).

Inverter 231 produces an output having the opposite polarity to that of amplifier 223 but of equal amplitude, which amplitude is about 18 volts peak to peak (which is the total supply voltage). Since the generated outputs are coupled through capacitors 220 and 221, both of which have a value of 120 pf, a resistance is produced of 25 ohms at 50 kHz and greater than 13 megohms at 100 Hz.

The peak current can be calculated as follows, if chest resistance (which is small compared to the capacitive reactance of capacitor 220 in series with capacitor 221), is neglected:

Capacitor 220 and capacitor 221 in series = 120 pf ÷ 2 = 60 pf. The balanced excitation voltage slope is:

$$\frac{18 \text{ volts} \times 2}{10 \ \mu s} \text{ or } 3.6 \text{ volts}/\mu s$$

then:

$$\frac{Q_p}{t} = \frac{CE}{t} = 60 \times 10^{-12} \text{ farads} \times 3.6 \text{ volts}/\mu s = 216 \times 10^{-12} \text{ coulombs}/\mu s$$

or
$216 \times 10^{-6}$ coulombs/second = 216 microamps peak.

The input from electrode 31 A is coupled through capacitor 236 to the positive input of amplifier 237, while the input from electrode 31 B is coupled through capacitor 238 to the positive input of amplifier 239, with the positive inputs of amplifiers 237 and 239 being connected with ground through resistor 240 and 241, respectively. The negative inputs of amplifiers 237 and 239 are connected to one another through resistors 243, while the outputs of amplifier 237 and 239 are fed back to the negative inputs through resistors 244 and 245, respectively, and each amplifier has a capacitor 246 and 247, respectively, in the circuit.

Amplifiers 237 and 239 thus comprise a balanced differential amplifier with reasonably high input impedance and wide bandwidth. The 50 kHz voltage drop across the chest impedance is coupled into the differential amplifier by means of capacitors 236 and 238, amplified by amplifiers 237 and 239, and finally peak to peak rectified by rectifier 204 at the input to amplifier 249.

Capacitor 251 is connected between the outputs of amplifier 237 and one side of rectifier 204, and resistors 252 and 253 are connected between the opposite sides of rectifier 204 and the input to amplifier 249. The positive input of amplifier 249 is connected with ground with capacitor 255 and resistor 256, while the output of amplifier 249 is fed back to the negative input through parallel connected resistor 258 and capacitor 259. Amplifier 249 is also connected to the +9 volt power source through resistor 260.

The output from amplifier 249 is a slowly varying voltage in accordance with the respiration rate, and this output is coupled through filter 206 (consisting of capacitor 262 and resistor 263 which set the lower 3 db frequency at 0.1 Hz) to the positive input of voltage follower 265. Voltage follower 265 has a capacitor 266 in the circuit, with the output from voltage follower 265 being fed back to the negative input through parallel connected resistor 267 and capacitor 268, and the output being also coupled through resistor 270 to amplifier 271.

The output from amplifier 271 is fed back to the negative input through parallel connected resistor 273 and capacitor 274. Amplifier 271 amplifies the respiration signal with a gain of 200, and also sets the upper 3 db frequency at 10 Hz by means of capacitor 274. The output of amplifier 271 is available as the impedance pneumograph wave.

The impedance across the chest changes greatly as the subject moves and generates large signals which tend to mask the respiration signal. It is thus necessary to incorporate techniques in the respiration rate pulse generating circuitry to discriminate against unwanted signals. The first technique incorporates an active second order low pass filter 210 with cutoff frequency at 1 Hz which reduces the active bandwidth from two decades (0.1 Hz-10 Hz) down to one decade. This filter is comprised of amplifier 276 and associated resistors 277, 278 and 279 and capacitors 281, 282 and 283. The second technique involves the use of a bipolar d.c. restorer 212 with rather soft limiting characteristic. This circuit, which consists of amplifier 285 and associated diodes 287 and 288, resistors 289, 290, 291, 292 and 293, and capacitors 294 and 295, greatly reduces the recovery time when a large extraneous signal is present.

The output from amplifier 285 is coupled to the negative input of amplifier 297 which acts as a threshold circuit with some hysteresis to convert the respiration signal into a squarewave. Amplifier 297 is connected through resistor 299 to the +9 volt power source, and the output of the amplifier is fed back to the positive input through resistor 300 with the positive input also being connected to ground through resistor 301.

The output from amplifier 297 is coupled through resistor 303 to the negative input of amplifier 304, with the output of amplifier 304 being fed back to the negative input through resistor 305 and with the negative input also being connected to the −9 volt power supply through resistor 306. Amplifier 304 is used to translate the squarewave voltage from 0 to +9 volts as required by the rate processor circuit, with the output being coupled through diode 308 having resistor 309 to ground connected thereat.

In a working embodiment of unit 43, the following impedance pneumograph specifications are utilized:

| Input Excitation | Current provided shall be 0.5 ma max at 50 ±5 kHz looking into subject impedances ranging from 100 to 1000 ohms. |
|---|---|
| Input Impedance | 10K ohms min. at 50 kHz and 10M ohms min. over 0 to 100 Hz range (when connected to subject impedance). |
| Input Circuit | Compatible with ECG input circuit hooked in parallel. True differential. |
| Frequency Response | −3db at 10 ±1 Hz. Minimum eventual rolloff of −6db/octave. |

In a working embodiment, and by way of example, the following components were used:

Amplifiers: 223, 231, 237 and 239—MLM308; 249, 271, 276, 297 and 304—L144/B; and 265 and 285—MLM108.

Diodes: 204 and 308—HPA2810; and 287 and 288—FD300.

Resistors: 226—51 k; 227—68 k; 228—390 k; 230—100 k; 232—10 k; 233—100 k; 240 and 241—510 k; 243—20 k; 244 and 245—200 k; 252, 253, 256 and 258—510 k; 260—10 M; 263 and 267—20 M; 270—51 k; 273—10 M; 277 and 278—4 M; 279—4.3 M; 289—39 M; 290 and 291—27 k; 292—1 M; 293—39 M; 299—10 M; 300—3.9 M; 301—30 k; 303—1 M; 305—510 k; and 306 and 309—1 M.

Capacitors: 220 and 221—120 pf; 224—10 pf; 225—120 pf; 234—10 pf; 236 and 238—39 pf; 246 and 247—10 pf; 251—100 pf; 255 and 259—330 pf; 262—0.082 μf; 266—100 pf; 268—0.001 μf; 274—1500 pf; 281—0.082 μf; 282—0.018 μf; 283—0.047 μf; 294—0.001 μf; and 295—100 pf.

As brought out hereinabove, the outputs from the ECG amplifier and cardiotachometer signal conditioner unit 41 and the impedance pneumograph and respiration rate signal conditioner unit 43 are coupled through switch 45 to heart/breath rate processor unit 47. This unit is shown in detail in FIGS. 5 and 6.

Rate processor unit 47 includes a single hybrid circuit which converts the time between pulses generated by either the ECG amplifier and cardiotachometer signal conditioner unit 41 or the impedance pneumograph and respiration signal conditioner unit 43 to determine the heart rate (in beats per minute) or respiration rate (in breaths per minute), respectively.

Processor unit 47 can be used for either heart rate or respiration rate providing the proper set of control frequencies are generated and coupled to the processor unit by clock circuit 51. In addition, the heart rate can be determined by beat-to-beat time or from the average of five consecutive heart beats through use of switch 29 (positioned for activation at the top of case 19). No analog techniques are required for the conversion, and since only digital components and techniques are used, no calibration adjustments are required. As a result, no components external to the hybrid package are necessary.

Past known techniques have commonly utilized a combination of analog and digital techniques and/or have utilized conventional printed circuit board construction. Such prior known techniques utilized larger components, consumed more power, required calibration adjustments, and were also subject to inaccuracies.

Figure 5:
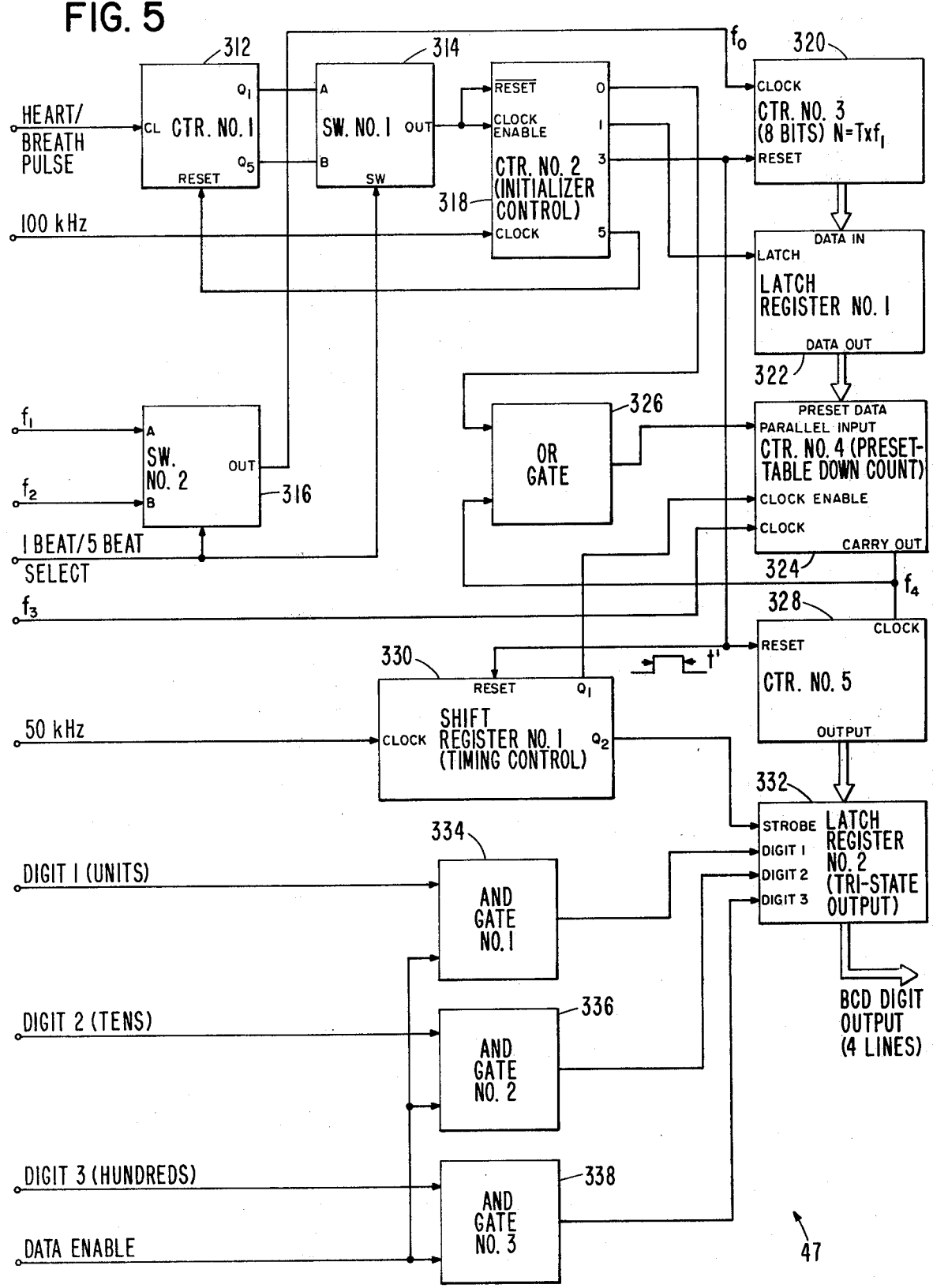
FIGS. 5 and 6 are block and schematic diagrams of the heart rate/breath rate processor unit as shown in FIG. 2.

FIG. 5 is a block diagram of the circuit of processor unit 47 and depicts the operation of the unit. Separate clock signals and either heart or breath pulses are required for operation, and the circuit can be used in telemetry or other data acqustion systems, although being particularly well adapted for use in this overall system.

As shown in FIG. 5, the heart/breath pulse from unit 41 or unit 43 is coupled to counter 312, which counter is an edge triggered counter that counts the number of heart or breath pulses received from unit 41 or unit 43. The outputs of counter 312 are connected with switch 314 so that counter 312 is active whenever one pulse or five pulses have been counted depending upon the count mode selected by switch 29, which switch is connected with switches 314 and 316.

Switch 314 is used to transfer either the selected one of the one pulse or five pulse output from counter 312 to the clock enable and $\overline{reset}$ inputs of a second (decade) counter 318. As shown, counter 318 also receives a 100 kHz clock input from clock input 51. Counter 318 works in conjunction with switch 314 to supply the correct frequency to the remaining circuitry for the one or five beat computation mode selected. Due to the time duration between breaths, it has been found, however, that breath rate is best computed only on a breath-to-breath basis.

The pulse transferred to counter 318 from switch 314 initiates operation of the remaining circuitry of processing unit 47 for processing of the heart/breath rate based on a total count N that is accumulated in a third (binary) counter 320 between the successive pulses occurring at counter 318. As shown, counter 320 receives a reset input from counter 318 and a clock pulse input $F_o$ from switch 316, which switch receives a pair of inputs $F_1$ and $F_2$ from clock unit 51.

The count N equals the period between heart/breath (less ten microseconds maximum and five microseconds minimum) times the frequency, $F_o$, that is counted by counter 320 for this period of time. The count N is then latched into latch register 322 which is used at the inputs of the fourth counter, or fourth counter 324 which is a presettable down counter. Latch register 322 receives a latch input from counter 318, while counter 324 receives a parallel input from counter 318 through OR gate 326. The count is preset into counter 324 at the beginning of processing and also whenever the counter has counted down to zero during processing. The result of this is that the carry out of counter 324 is a frequency $F_4$ given by $F_4 = F_3/N = F_3/(T \times F_o)$, where T=heart/breath beat period in seconds, $F_3 = 50$ kHz, and $F_o = 166.\overline{6}$ Hz or $33.\overline{3}$ Hz for heart rate and 25 Hz for respiration rate, for example.

A fifth counter 328, which is a BCD counter with a count capacitor of 199, counts the frequency, $F_4$ for a period of time $t^1$ which equals 0.2 seconds for heart rate and 0.24 seconds for respiration rate. This time period, $t^1$ is generated by shift register 330 (which receives an input $F_3 = 50$ KHz from clock unit 51) and a 10 Hz (heart rate) or $8.\overline{3}$ Hz (respiration rate) input frequency is coupled to counter 324 from clock unit 51. At the end of $t^1$, a second output of shift register 330 latches the count accumulated by counter 320 into latch register 332, which register is a tri-state output latch register.

This tri-state output (which is coupled to LCD driver unit 55 as shown in FIG. 2) allows all three digits to be wired together to form one four-line BCD output. The digit output enable lines are controlled by LCD driver unit 55 with the outputs therefrom being coupled to latch register 332 through AND gates 334, 336 and 338, as shown in FIG. 5.

The resultant output count R that is displayed is equal to:

$$R = F_4 \times t^1 = \frac{F_3 \times t^1}{N} = \frac{F_3 \times t^1}{F_o \times T} = \frac{60}{T} \text{ counts/second} = \frac{1}{T} \text{ counts/minute, where } T \text{ is units of seconds}$$

The calculation of heart rate or breath rate is based on dividing the period of the event into a constant such that the result is equal to the rate in beats or breaths per minute. The foregoing describes how this is done digitally. Rate processor 47 calculates heart rate from 40 to 200 beats per minute with an accuracy of one beat per minute, and calculates breath rate from 6 to 24 breaths per minute with an accuracy of one breath per minute. In addition, since CMOS devices are utilized, the unit has low power requirement.

Figure 6:
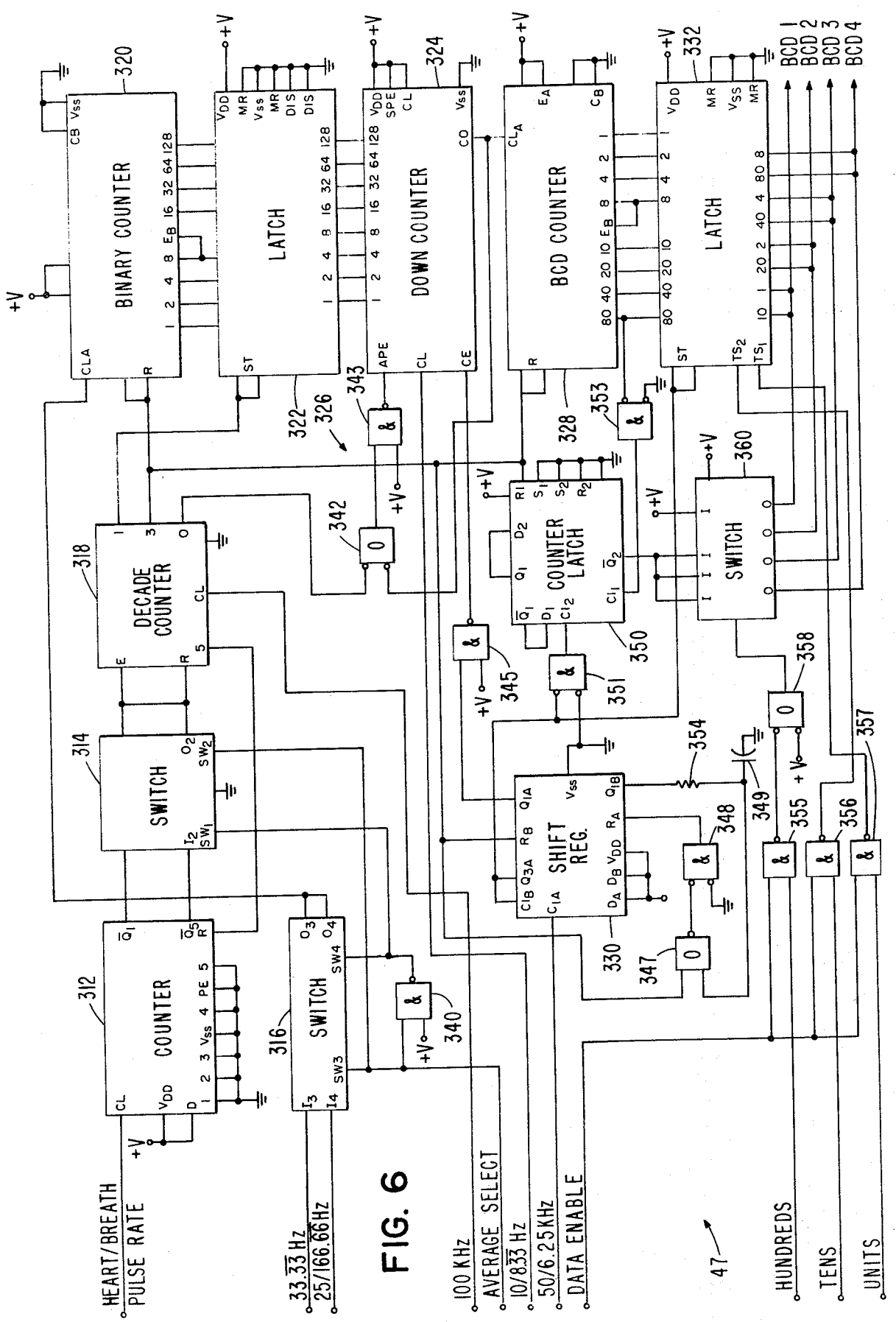

FIG. 6 is an expanded block schematic diagram showing rate processor 47 in more detail than does FIG. 5. The circuit of FIG. 6 operates in the same manner as that of FIG. 5, but has been implemented in a slightly different manner.

With respect to switch 316, the average select (i.e., one beat or five beats) input is coupled thereto directly and through NAND gate 340. With respect to OR gate 326, this has been implemented through use of negated input NOR gate 342 and NAND gate 343, as shown in FIG. 6.

As also shown in FIG. 6, the output from shift register 330 supplies a clock input to down counter 324 through NAND gate 345, while the reset input from decade counter 318 is coupled both directly to the $R_B$ input of the circuit and to the $R_A$ input through NOR gate 347 and negated input AND gate 348. As shown, one input to NOR gate 347 is connected with ground through capacitor 349.

In addition, in the circuit as shown in FIG. 6, the output from shift register 330 connected to latch 332 is also coupled to counter/latch 350 through negated input NAND gate 351, with the output of counter/latch 350 being coupled to the reset input of BCD counter 328. An output from BCD counter 328 is then coupled back to counter/latch 350 through negated input AND gate 353. Shift register 330 also has a resistor 354 from input $Q_{1B}$ to capacitor 349 (to ground).

As also shown in FIG. 6, the gating arrangement for gating the data select information to processor unit 47 from LCD driver unit 55 utilizes NAND gates 355, 356 and 357 with gate 355 being coupled through negated input OR gate 358 to switch 360, which switch is connected with counter/latch 350 and latch 332.

In a working embodiment of unit 47, the following CMOS components (except for capacitor 349 and resistor 354), by way of illustration, have been utilized:

Resistor 354—100 k.
Capacitor 349—82 pf.
Counters: 312—4018; 318—4017; 320—4520; 324—40103; 328—4518; and 350—4013.
Switches: 314 and 316—4016.

Registers: 322—4508; 330—4015; and 332—4508.
Gates: 340—4011 B; 342—4011; 343—4011; 345—4011; 347—4001; 348—4001; 351—4001; 353—4001; 355—4011 B; 356—4011 B; 357—4011 C; and 358—4011.

In addition, the frequencies utilized for heart beat processing are 33.33 Hz, 166.66 Hz, 100 kHz, 50 kHz and 10 Hz, while the frequencies utilized for breath rate processing are 25 Hz, 100 kHz, 6.25 kHz and 8.33 Hz.

The temperature monitor circuit 49, utilized in this invention and as shown in FIG. 2, provides temperature information on data lines to LCD driver unit 55, while the LCD driver unit provides digit select information to the temperature monitor.

Figure 7:
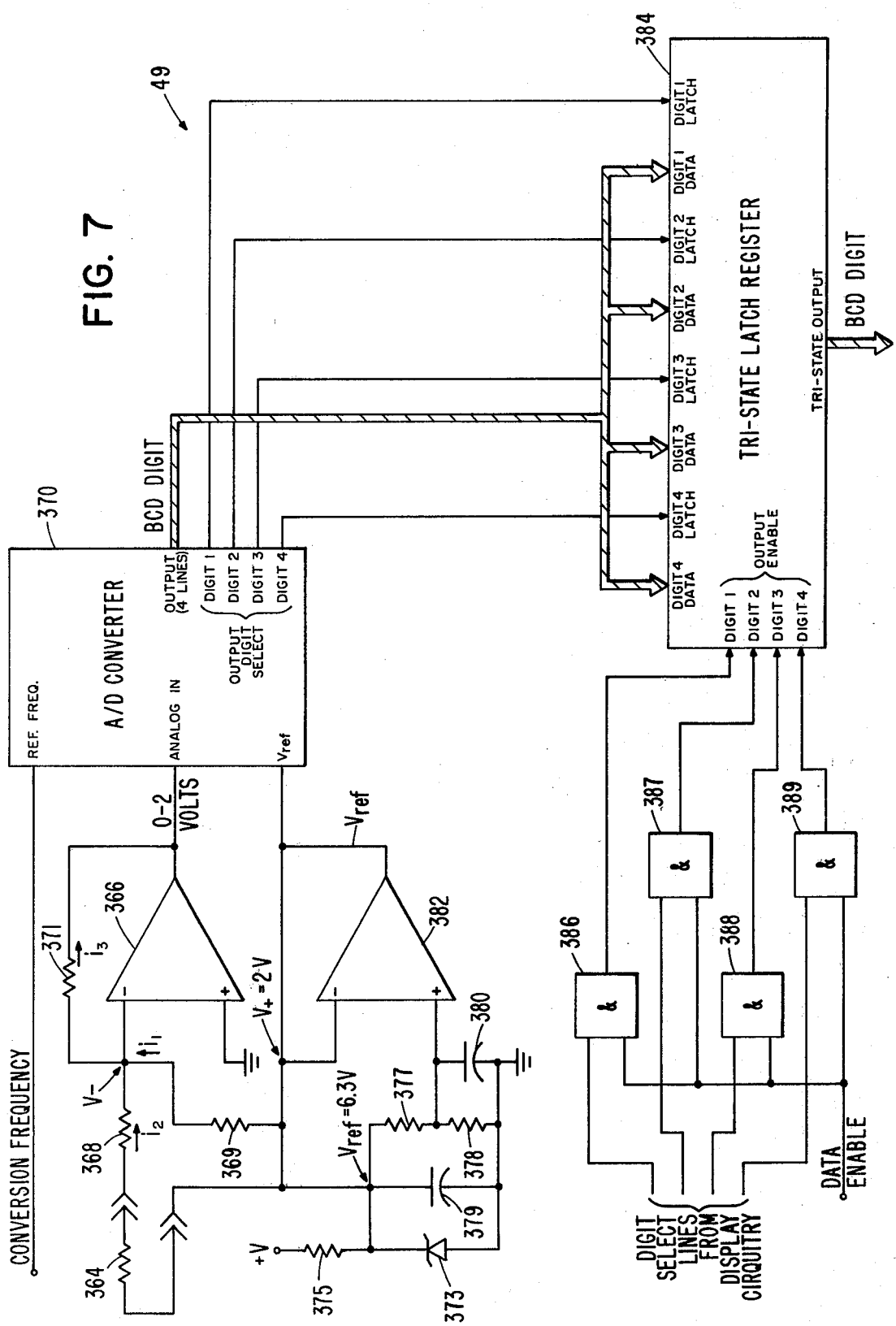
FIGS. 7 and 8 are block and schematic diagrams of the temperature monitoring unit as shown in FIG. 2.
Figure 8:
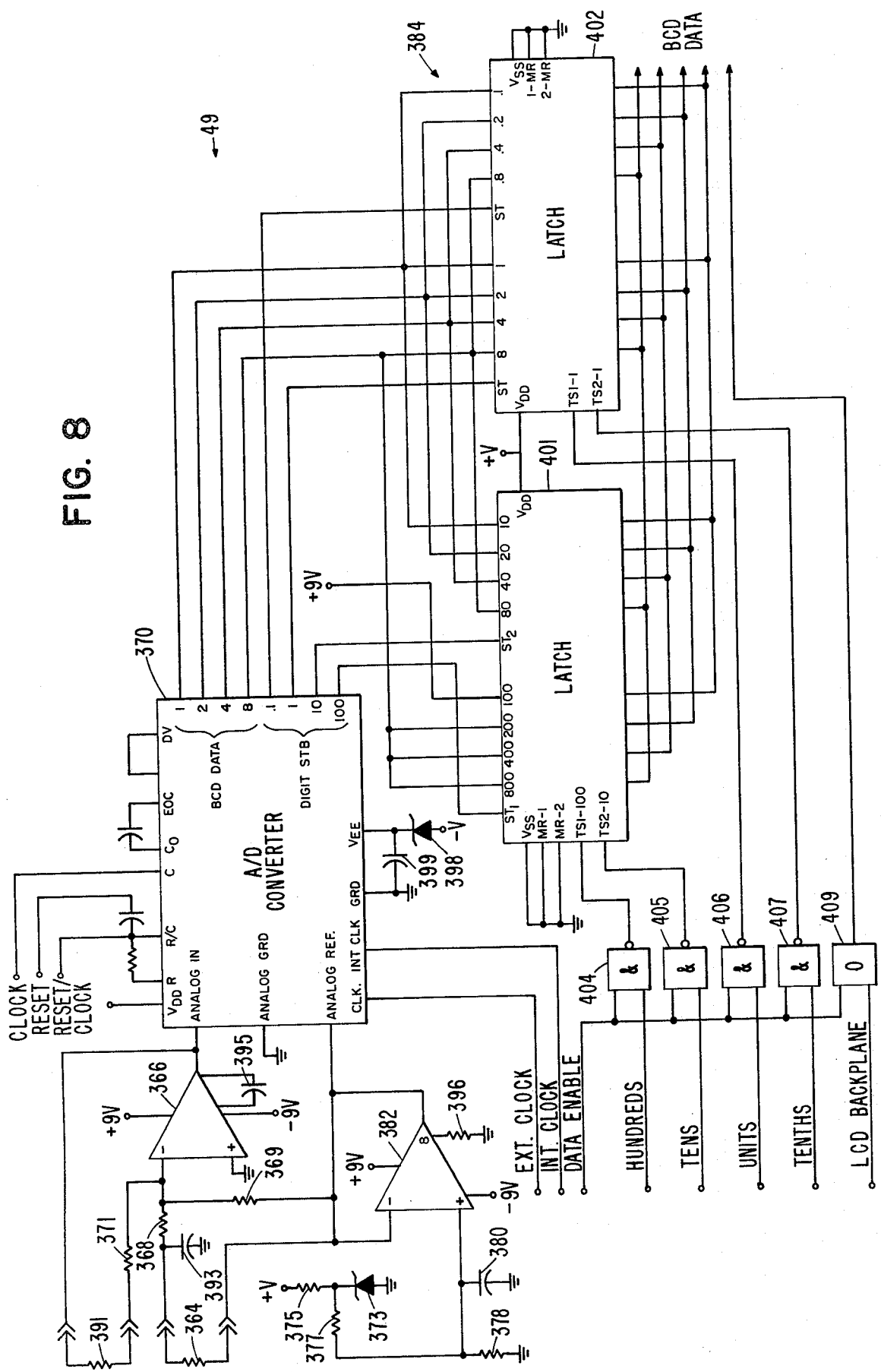

Temperature monitor unit 49 is shown in detail in FIGS. 7 and 8. As shown, this unit is a single hybrid circuit capable of sensing temperature, using a thermistor probe 364, and providing a digital output signal compatible for use by LCD driver unit 55 in the same manner as the rate processor unit 47 outputs are utilized by the driver unit.

Since the thermistor is a non-linear device, this unit includes circuitry for linearizing the temperature indications from the thermistor and also to make these indications insensitive to changes in supply voltages and/or component value. Heretofore, various analog-to-digital conversion schemes have been utilized, as have standard printed circuit techniques. These schemes and techniques, however, have not allowed the use of sufficiently small size components in a circuit having low power requirements.

Temperature monitor circuit 49 produces a binary coded decimal (3½ digit) output corresponding to the temperature of small thermistor probe 364, and the circuit is in hybrid form. Temperature monitor circuit 49 utilizes clock inputs (from clock unit 51) and sensed temperatures may be displayed on LCD display 25, with the temperature monitor also being operable as a separate unit if a frequency determining capacitor and display are added, and it may also be used in telemetry or data acquisition systems.

FIG. 7 is a block diagram of temperature monitor circuit 49 depicting the operation of the circuit. As shown, one side of thermistor 364 is connected to the negative input of operational amplifier 366 through resistor 368, while the other side of thermistor 364 is connected with a $V_{ref}$ point. Thermistor 364 also has a resistor 369 connected in parallel therewith.

The output voltage of operational amplifier 366 is equal to:

$$V_{out} = -V_{ref}R_F \left( \frac{1}{R_T + R_p} + \frac{1}{R_B} \right).$$

This output is coupled as analog data input to A/D converter 370, and is fed back to the negative input through resistor 371.

Zener diode 373 is connected at one side to ground and at the other side through resistor 375 to a +V power supply with the junction of Zener diode 373 and resistor 375 being a $V_{ref}$ point ($V_{ref}$=6.3 volts). In addition, Zener diode 373 has series connected resistors 377 and 378 and capacitor 379 connected in parallel therewith, with resistor 378 also having a capacitor 380 in parallel therewith, and the junction of resistors 377 and 378 being connected with the positive input of a second operational amplifier 382 (the negative input of which is connected to the $V_{ref}$ point).

Zener diode 373 and operational amplifier 382 form the voltage reference required for temperature computation. By using this reference voltage, the input to both operational amplifier 366 and the analog-to-digital (A/D) converter 370, any changes in $V_{ref}$ due to small changes in the power supply voltage minimizes the effect on the computed value of temperature. Resistors 368 and 369 are used to linearize the thermistor dependence on temperature. The values are chosen to minimize the error of $V_{out}$ at 98.6° Fahrenheit (37° C.). A three point linearization of the thermistor dependence of resistance to temperature curve has been made at 32° C., 37° C. 37° C. and 42° C. to produce minimum error in the desired region of operation. This technique reduces the errors in measured temperature to within one count, or 0.1%° F. A part of this linearization process is the forming of $V_{out}$ so that when converted by the analog/digital converter, the resultant digital output is a direct reading of temperature in degrees Fahrenheit.

The output of analog/digital converter 370 is multiplexed so that each of the four digits is presented at the same four bit output. The particular digit present at the output is indicated by the output digit select lines which are used to latch the data into the appropriate location of tri-state latch register 384. Tri-state register 394 outputs allow all four digits to be wired together to form one four-line BCD output. The digit output enable lines are controlled by the display logic control of LCD driver unit 55 through AND gates 386, 387, 388 and 389.

The variation of a thermistor with temperature can be approximated by $$R_T = \frac{a}{T-b} - p$$

where, T is temperature and a, b and p are determined to give good agreement with the temperature-resistance curve.

The approximation allows a three point approximation to the thermistor resistance curve by solving for a, b and p at selected temperatures.

Solving this equation for temperature gives $$T = \frac{a}{R_T + p} + b.$$

The output voltage of operational amplifier 366 in FIG. 7 is:

$$V_{out} = \left(\frac{R_F}{R_T + R_p} + \frac{R_F}{R_B}\right) V_{ref}$$

If we let:

$$a = KV_{ref}R_F$$

$$b = KV_{ref}(R_F/R_B) \text{ (where K} = 100° \text{ F./volt)}$$

$$p = R_p$$

then $$T = KV_{out}$$

As can be seen, the temperature as indicated by the analog-digital converter does not depend on the actual reference voltage since the converter utilizes $V_{ref}$ as a scaling factor in computing $V_{out}$. Therefore, the temperature reading is very nearly independent of supply voltage.

Sensitivities of the output voltage (temperature reading) as a function of component values were calculated to all be equal to or less than one for the circuit shown in FIG. 7.

Temperature monitor circuit 49 can be adjusted to a given thermistor by selection of an external resistor 391 (see FIG. 8) in series with the feedback resistor 371 so that the resulting resistance is the series combination of these two resistors. This allows a 3% variation in temperature reading. Selecting the external resistor to 1% tolerance allows a calibration of the temperature to within 0.1%. Temperature readings are within a 1% of a straight line through this calibration point for the temperature range of 30° F. to 110° F.

Temperature monitor unit 49 is designed to be used with external clock inputs from clock unit 51 and display circuits through LCD driver unit 55. The clock may be eliminated, however, by utilizing a timing capacitor on the temperature monitor's internal clock circuit. The circuit is also suitable for telemetry and data acquisition systems without the use of an external display.

FIG. 8 shows an expanded block and schematic diagram of the temperature monitoring circuit 49 with implementation slightly different from that of FIG. 7. As shown, a capacitor 393 is included at one side of resistor 368, amplifier 366 is shown to include a capacitor 395 in the circuit, amplifier 392 is shown connected with ground at pin 8 through resistor 396, and A/D converter 370 has a Zener diode 398 connected with the $V_{EE}$ input and a $-V$ power source with the junction also having a bypass capacitor 399 to ground thereat. In addition, as shown in FIG. 8, tristate latch register 394 includes a pair of interconnected latches 401 and 402 with the digit select inputs being coupled through NAND gates 404, 405, 406 and 407. An additional input entitled LCD backplane is also coupled through exclusive OR gate 409, which gate also receives a data enable input.

The temperature monitor circuit as shown in FIG. 8 operates in essentially the same manner as described in connection with FIG. 7. In a working embodiment, the following components, by way of example, were utilized:

Amplifiers: 366—MLM108; and 382—MC1776C.
A/D Converter 370—MC14433.
Zener Diodes: 373 and 398—LVA450.
Latches: 401 and 402—MC14011.
HEX Inverter 409—MC14070.
NAND gates: 404, 405, 406 and 407—MC14011.
Registers: 368—46.55k; 369—362.8k; 371—39k; 375—33k; 377—150k; 378—100k; 391—1.37k; and 396—390k.
Capacitors: 380—0.01 µf; 393—0.047 µf; 395—100pf; and 399—0.01 µf.

Figure 9:
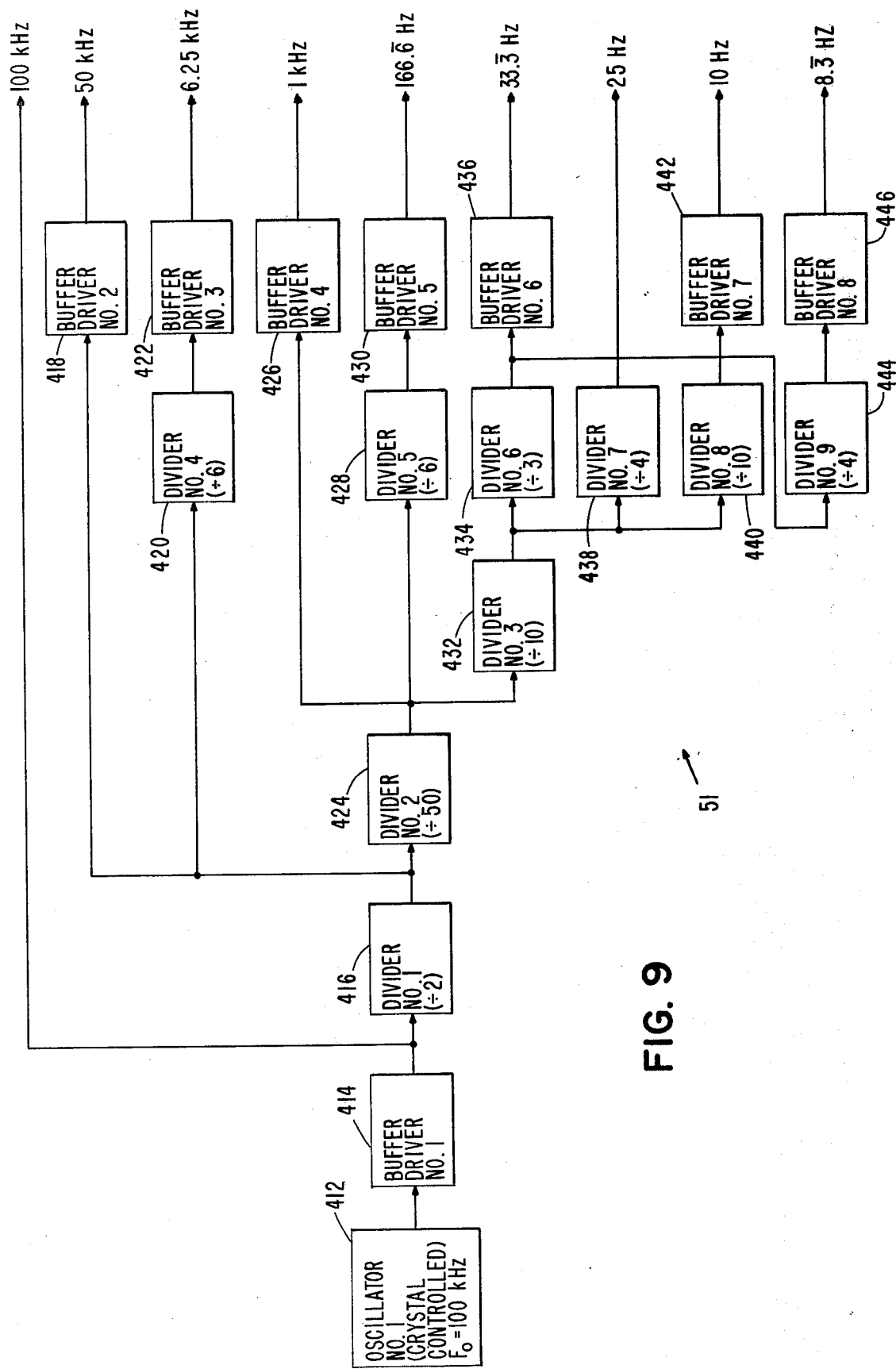
FIGS. 9 and 10 are block and schematic diagrams of the clock unit as shown in FIG. 2.
Figure 10:
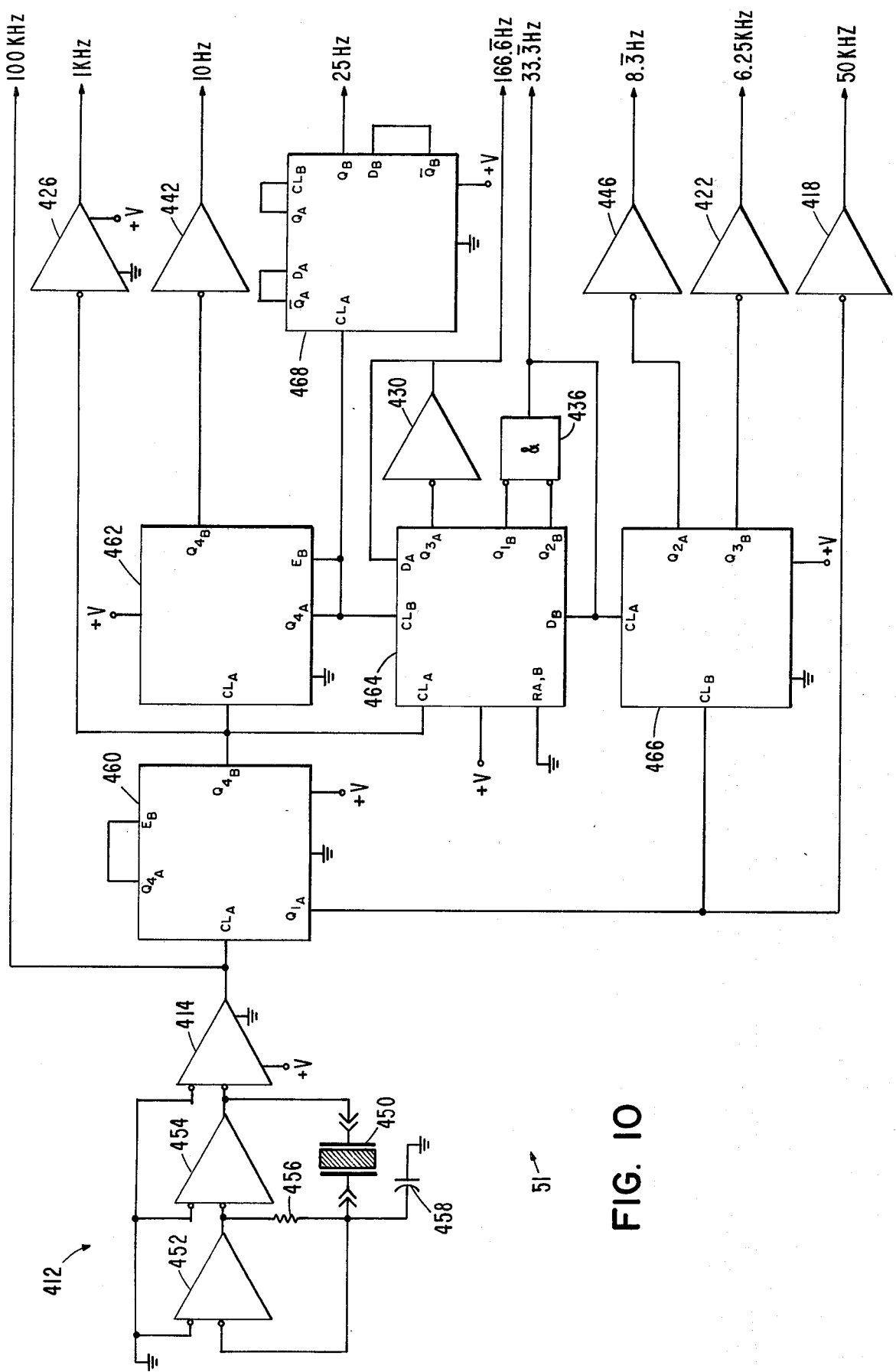

Clock unit 51 is shown in FIGS. 9 and 10. As shown, clock 51 is a single hybrid circuit providing all required control frequencies needed for vital sign monitoring system 17. In addition, the circuit will operate as a unit with the use of a small, external, frequency determining crystal (and particularly, a Reeves-Hoffman RH-170 crystal which has small physical dimensions).

FIG. 9 is a clock diagram of clock unit 51 and depicts its operation. Crystal controlled oscillator 412 provides an output signal ($F_o = 100$ kHz $\pm 0.01\%$) and this signal is coupled through buffer driver 414 to provide a 100 kHz output. The 100 kHz output is also coupled to a $\div 2$ divider 416, the output of which divider is coupled through a second buffer driver 418 to provide a 50 kHz output signal, is coupled through a $\div 6$ divider 420 and a third buffer driver unit 422 to provide a 6.25 kHz output signal, and is coupled to a $\div 50$ divider 424.

The output from $\div 50$ divider 424 is coupled through a fourth buffer amplifier 426 to provide a 1 kHz output signal, is coupled through a $\div 6$ divider 428 and a fifth buffer driver 430 to provide a $1.66\overline{6}$ Hz output signal, and is coupled to $\div 10$ divider 432. The output of $\div 10$ divider 432 is coupled through $\div 3$ divider 434 and a sixth buffer driver 436 to provide a $33.\overline{3}$ Hz output signal, is coupled through $\div 4$ divider 438 to provide a 25 Hz output signal, and is coupled through $\div 10$ divider 440 and a seventh buffer driver 442 to provide a 10 Hz output signal. In addition, the output from $\div 3$ divider 434 is also coupled to $\div 4$ divider 444, the output of which is coupled through an eighth buffer driver 446 to provide a $8.\overline{3}$ Hz output signal.

Implementation of the clock unit 51 is shown in FIG. 10. As shown, 100 kHz crystal 450 is connected in circuit with negated input amplifiers 452 and 454 with resistor 456 being connected between the junction of the amplifiers and one side of the crystal, which also has a bypass capacitor 458 to ground thereat.

Buffer driver 414 is also shown as a negated input amplifier, as are buffer drivers 418, 422, 426, 430, 442 and 446, while buffer driver 436 is shown as a negated input AND gate. The dividers (and amplifiers) are all CMOS units with CMOS circuit 460 (receiving the output from buffer driver 414) including $\div 2$ divider 416 and $\div 2$ divider 424 (as shown in FIG. 9), CMOS unit 462 (connected with CMOS unit 460) including $\div 10$ divider 432 and $\div 10$ divider 440 (as shown in FIG. 9), CMOS unit 464 (connected with CMOS unit 462) including $\div 6$ divider 428 and $\div 3$ divider 434 (as shown in FIG. 9), CMOS unit 466 (connected with CMOS unit 464) including $\div 6$ divider 420 and $\div 4$ divider 444 (as shown in FIG. 9), and CMOS unit 468 (connected with CMOS unit 462) including $\div 4$ divider 438 (as shown in FIG. 9).

In a working embodiment of the clock unit 51 as shown in FIG. 10, the following components, by way of illustrative example, have been utilized:

Amplifiers: 414—4001; 418, 422, 426 and 430—4049; 436—4001; 442 and 446—4049; and 452 and 454—4001.

CMOS circuits: 460 and 462—4518; 464—4015; 466—4520; and 468—4013.

Resistor 456—47k.

Capacitor 458—180pf.

Figure 12A:
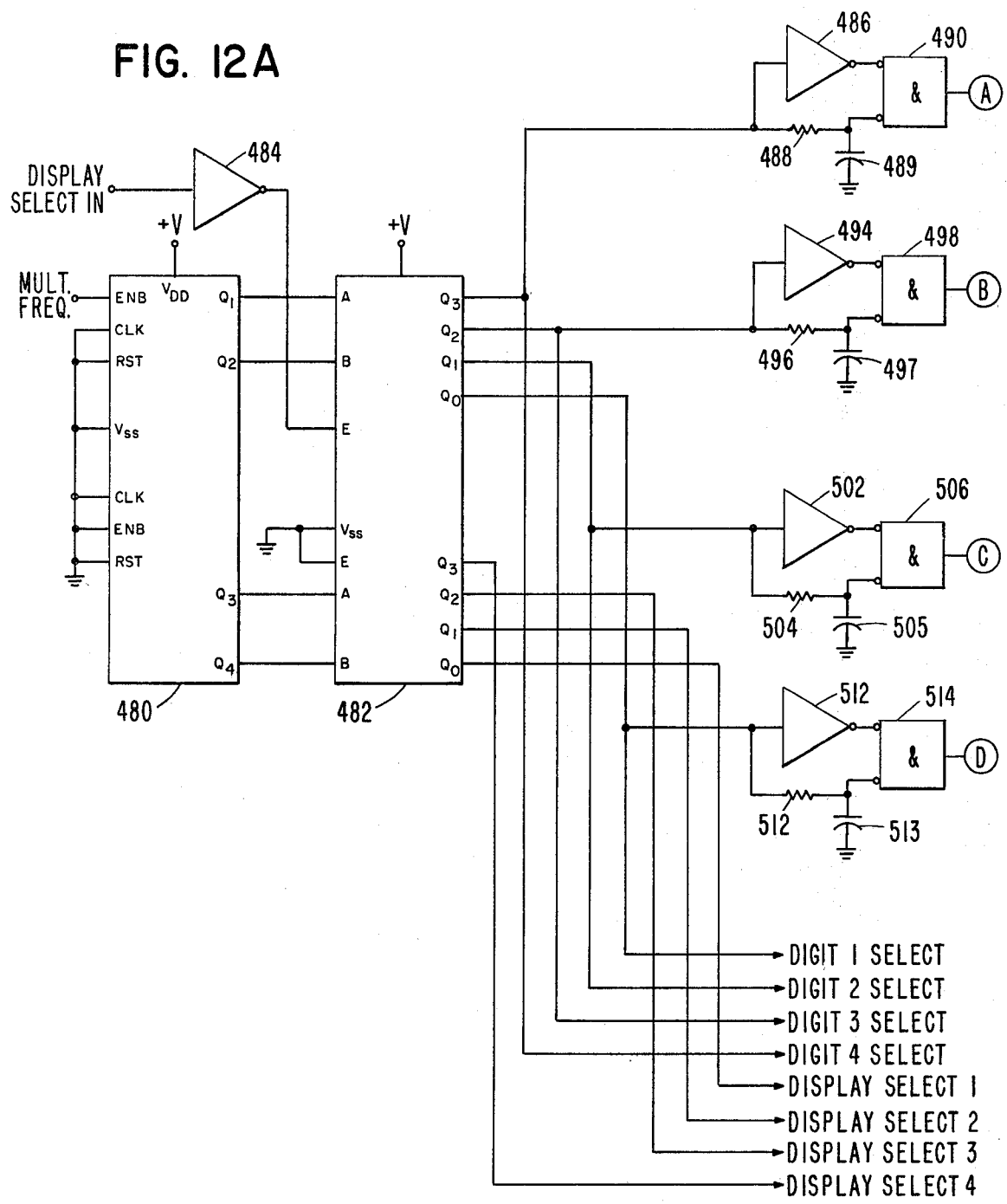
FIGS. 12 A and B constitute a schematic and block diagram of the LCD driver unit as shown in FIG. 2.
Figure 12B:
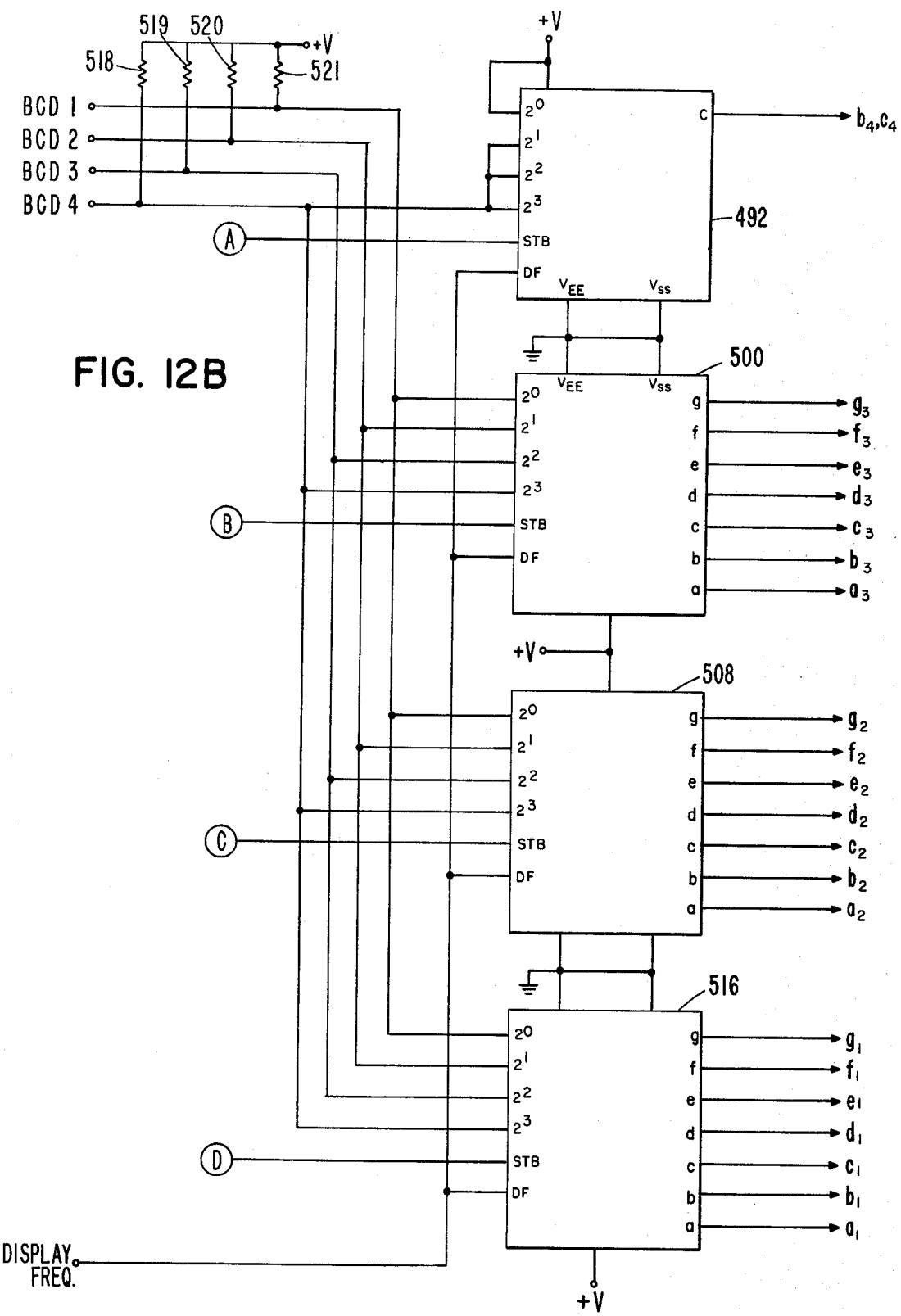

The overall vital signs processor data output circuitry is shown in FIG. 11, while FIG. 12 shows LCD driver unit 55 utilized in conjunction therewith.

Unit 55 is suitable for displaying one of various configurations of liquid crystal displays (LCDs) 25, and utilizes circuitry so that the display system is flexible to allow different display formats to be used with a minimum of interconnecting lines (prior techniques were commonly compatible only with seven-segment LCD displays and have required a separate seven-segment LCD display for each device having a digit output).

LCD driver unit 55 is in hybrid form and consists of a package that can be utilized in several modes to display the vital signs supplied thereto (or could display data from other systems connected thereto).

FIG. 11 shows the general configuration of the data output circuitry used in all of the vital signs processors discussed hereinabove. The primary goal of such an output configuration is two-fold, namely; (1) to reduce the number of interconnection lines required between the vital signs processors and the display system, and (2) to provide the flexibility required for several types of display systems.

The first goal is realized by using tri-state output latch registers (as described hereinbefore and generally designated by the numeral 472 in FIG. 11) and WIRE-ORing each level of the BCD data lines together so that only four BCD data lines need be outputted from each processor, and furthermore, by WIRE-ORing the four BCD data output lines of all the vital signs processors together so that only four interconnection lines are required external to the processor packages to transfer all the data from the processors to the display system.

With this configuration, only one digit of information can be transferred at any given time. As such, a separate digit select line is required for each digit of BCD data to be displayed. This implies that for a display system which simultaneously displays all sixteen digits of a vital signs system, twenty interconnection lines are required between the processors and the display system.

The remaining control line in the data output circuit configuration (as shown in FIG. 11) is the digits select enable line (which includes NAND gates 474, 475 and 476) which line, in conjunction with the other I/O data lines already discussed, helps realization of the second goal of flexibility. Finally, it should be noted that the data I/O system being used exhibits the inherent flexibility that will more easily allow interfacing this data to parallel-to-serial converters for transmission of data long distances over a single twisted-pair line, and also will allow simple interfacing to a micro-processing or minicomputing system should such requirements arise.

FIG. 12 is a block and schematic diagram of the LCD display driver circuitry 55. This circuitry is capable of receiving and displaying three and one-half digits of data, and is the only hybrid package required for a four digit LCD.

As shown in FIG. 12, the multiplexed frequency input is coupled to the enable input of integrated circuit 480 (a $\div 16$ counter), which circuit is interconnected with a second integrated circuit 482 (which includes a pair of one of four decoders). The display select input is coupled to the enable input of integrated circuit 482 through inverter 484.

A first output ($Q_3$) from integrated circuit 482 is coupled through inverter 486 and resistor 488 (having bypass capacitor 489 to ground thereat) to the inputs of negated input AND gate 490, the output of which is coupled to integrated circuit 492. In like manner, a second output ($Q_2$) from integrated circuit 482 is coupled through inverter 494 and resistor 496 (having bypass capacitor 497 to ground thereat) to the inputs of negated input AND gate 498, the output of which is coupled to integrated circuit 500; a third output ($Q_1$) is coupled through inverter 502 and resistor 504 (having a bypass capacitor 505 to ground thereat) to the inputs of negated input AND gate 506, the output of which is coupled to integrated circuit 508; and a fourth output ($Q_0$) is coupled through inverter 510 and resistor 512 (having a bypass capacitor 513 to ground thereat) to negated input AND gate 514, the output of which is coupled to integrated circuit 516 (the $Q_0$-$Q_3$ outputs also provide Digit 1-4 select outputs as shown in FIG. 12, while a second set of $Q_0$-$Q_3$ outputs from integrated circuit 482 provides display select 1-4 outputs as also shown in FIG. 12).

As also shown in FIG. 12, the BCD inputs (1, 2, 4 and 8) are coupled to integrated circuit 500, 508 and 516, while the BCD 8 input is coupled to integrated circuit 492. All of the BCD inputs (1, 2, 4 and 8) are connected with a $+V_o$ power supply through resistors 518, 519, 520 and 521, respectively.

Integrated circuits 492, 500, 508 and 516 are BCD to LCD display decoders. The outputs from integrated circuits 500, 508 and 516 are segment outputs to drive the LCDs 25.

In a working embodiment, the following components, by way of illustrative example, have been utilized for LCD driver unit 55:

Integrated Circuits: 480 and 482—4520; and 492, 500, 508 and 516—4056.

Inverters: 484, 486, 494, 502 and 510—4049.

Negated Input AND gates: 490, 498, 506 and 514—4001B.

Resistors: 488, 496, 504 and 512—100k; and 518, 519, 520 and 521—2M.

Capacitors: 489, 497, 505 and 513—27 pf.

Circuitry 55 also contains control functions to properly synchronize four identical packages for controlling a sixteen digit LCD display. This, by far, is the most difficult display representation of those possible for the vital signs system and such a system is shown in block form in FIG. 13.

As shown, five different LCD displays 530, 531, 532, 533 and 534 are utilized, with these displays being driven by four LCD driver units 535, 537 and 538.

Figure 13:
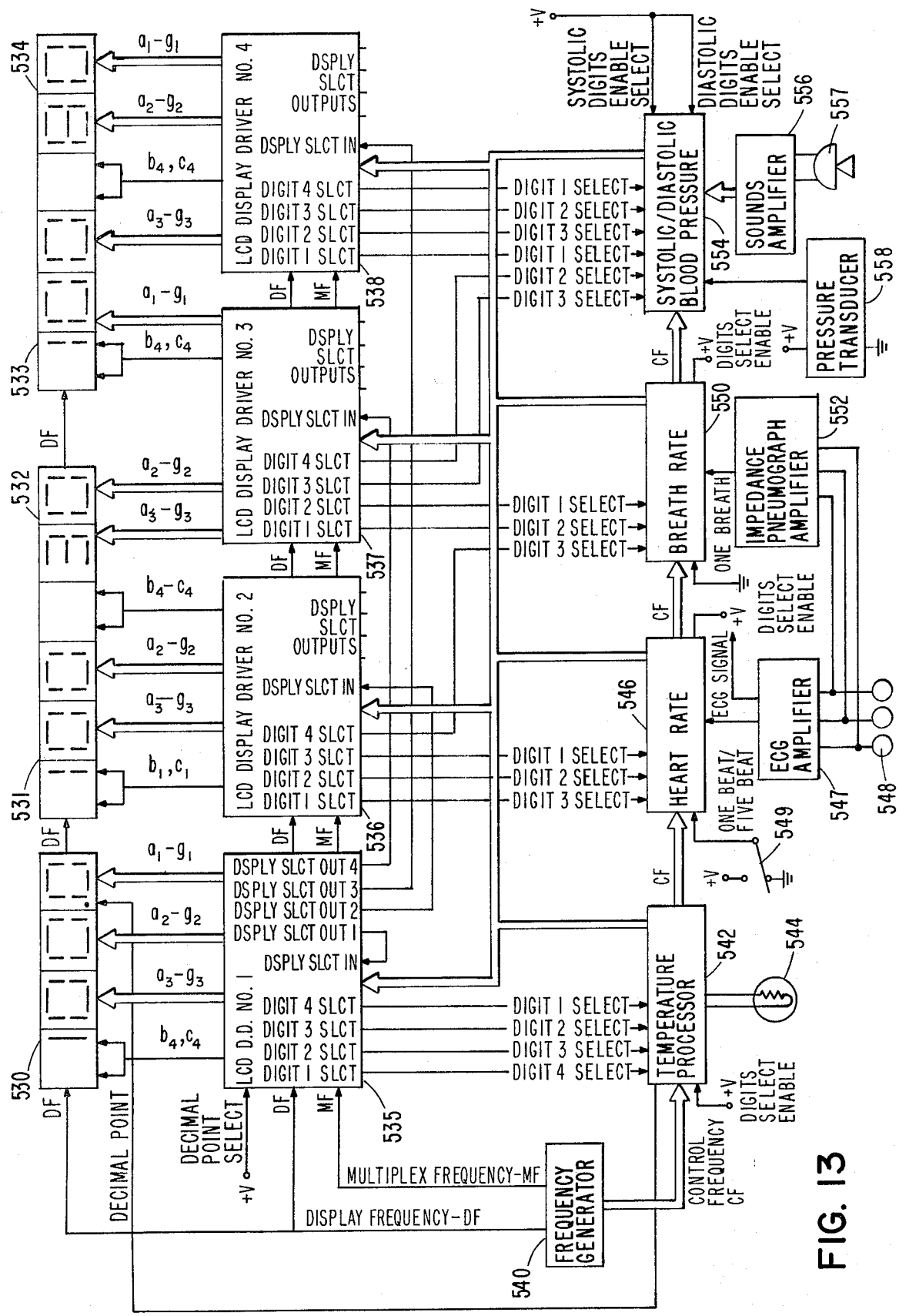
FIG. 13 is a block diagram illustrating the expansion of the vital signs monitoring system of this invention.

A frequency generator, or clock, unit 540 provides the necessary timing functions (and this clock may be like that of clock unit 51 as described hereinabove). As processors, the system, as shown in FIG. 13, includes a temperature processing unit 542 (having thermistor 544 connected therewith), a heart rate processor unit 546 (having an ECG amplifier 547 and electrodes 548, as well as a one beat/five beat selector switch 549, connected therewith), a breath rate processor unit 550 (having an impedance pneumograph amplifier 552 and electrodes 548 connected therewith), and a systolic/diastolic blood pressure unit 554 (having a sounds amplifier 556 and microphone 557, a pressure transducer 558, and systolic and diastolic digits enable selects connected therewith). Temperature processor 542 and heart rate and breath rate processors 546–550 may be identical to temperature processor unit 49 and heart/breath rate processor unit 47 discussed hereinbefore, while the systolic/diastolic blood pressure unit is patterned thereafter.

It should be noted that in the embodiment of the invention as shown in FIG. 13, the four display select output lines of the LCD display driver 535 are used to synchronize all four drivers together so that only one digit of vital sign data will be placed on the BCD data lines at one time. The display select output lines of the remaining LCD display drivers are not used. Also, it is to be noted that the digits select enable lines of each vital signs processor are not required for this display configuration and they are therefore wired to the system V+ bus lines. As a result, only twenty interconnect lines are required between the vital signs processors and the display circuitry.

As the multiplexed frequency sequences the divide-by-sixteen binary counters (480 as identified in FIG. 12) in each of the LCD display drivers, one of four display select lines are active high as a result of decoding the most significant two bits of the binary counter with the second one of four decoder (lower portion of integrated circuit 482 as shown in FIG. 12).

By routing the display select lines to each of the four LCD display drivers-display select in lines, one of the LCD display drivers has an active high digit select line corresponding to the count of the least significant two bits of the binary counter which is decoded with the first one of four decoder (top portion of integrated circuit 482 as shown in FIG. 12).

The result of this action is that, as the binary counter cycles through all possible sixteen count states, each of the sixteen digit select lines in the four LCD driver packages as shown in FIG. 13, are activated in turn. These digit select lines are routed to each of the digit select input lines of the vital signs processors, and to the strobe inputs of the BCD to LCD display decoders. Thus, for every full cycle of the counter ($\div 16$ circuit 480) states, each of the sixteen digits to be displayed are latched into the latch of the proper LCD display driver, and are in turn displayed at the proper LCD digit in the display.

The display circuits display the following vital signs to the resolution indicated:

1. Body temperature—$3\frac{1}{2}$ digits and decimal point required,
2. Heart Rate—$2\frac{1}{2}$ digits required,
3. Breath Rate—2 digits required,
4. Systolic Blood Pressure—$2\frac{1}{2}$ digits required,
5. Diastolic Blood Pressure—$2\frac{1}{2}$ digits required.

The $\frac{1}{2}$ digit refers to the most significant digit which requires a one or blank display only.

In operation, the electrodes 31 are placed on a patient, and the vital sign then to be monitored is selected by the operator along with the selection of internal batteries (which are within case 19) or external power, and the one or five averaged beat (where heart beat is to be monitored). The system will then automatically display the vital sign then being monitored on LCDs 25. If a plurality of signs are to be monitored, it is then only necessary in each case to rotate the selector switch 23 to locate the vital sign then to be monitored.

As can be appreciated from the foregoing, this invention provides an improved vital signs monitor having improved circuitry to effect the desired end.

What is claimed is:

1. A system for monitoring vital physiological signs, said system comprising:
   a plurality of sensing means for sensing predetermined vital physiological signs and responsive thereto providing output signals indicative thereof;
   a plurality of signal processing means connected with different ones of said sensing means to receive said output signals therefrom, each of said processing means including data output circuitry means having tri-state output latch register means for providing BCD data output on four data lines; and
   indicating means connected to receive said BCD data output on said four data lines and indicating said predetermined vital physiological signs sensed by said sensing means.

2. The system of claim 1 wherein said plurality of sensing means includes at least heart, breath and temperature sensors each of which produces separate output signals indicative of the vital sign sensed.

3. The system of claim 2 wherein said plurality of signal processing means includes a first processor for sensing the outputs from said heart and breath sensors, and a second processor for sensing the outputs from said temperature sensor.

4. The system of claim 1 wherein the corresponding ones of each of said four data lines of each of said plurality of processing means are connected to one another so that said indicating means is connected with said plurality of said processing means by only four data lines.

5. The system of claim 4 wherein said indicating means includes select means for providing select information to said plurality of processing means for selecting the information to be then indicated by said indicating means.

6. The system of claim 1 wherein said indicating means includes liquid crystal devices for visually displaying sensed vital signs, and LCD driver means connected with said data lines for effecting said display.

7. The system of claim 1 wherein said system includes timing means connected with said plurality of processing means and with said indicating means.

8. The system of claim 7 wherein said timing means includes a clock circuit for providing all frequencies needed by said processing means and said indicating means for timing purposes.

9. An integrated system having a plurality of hybrid circuits monitoring vital physiological signs and displaying the same, said system comprising:
a plurality of sensing means sensing predetermined vital physiological signs and responsive thereto producing output signals indicative thereof;
a plurality of signal processing means each of which is connected with predetermined ones of said sensing means to receive said output signals therefrom and responsive thereto providing BCD output data with each of said signal processing means including data output means whereby said BCD output data from each of said signal processing means is outputted on four data lines;
data coupling means including four data lines connected with corresponding ones of each of said four data lines of said signal processing means;
LCD driver means connected with said four data lines of said data coupling means to receive said BCD output data from said signal processing means, said LCD driver means including select means connected with said signal processing means to select the BCD output data to be coupled to said LCD driver means on said data lines;
timing means connected with said signal processing means and said LCD driver means for providing timing signals thereto; and
LCD display means connected with said LCD driver means for displaying the sensed vital sign information then coupled to said LCD driver means through said data lines.

10. The system of claim 9 wherein said sensing means includes heart, breath and temperature sensors, and wherein said plurality of signal processing means includes heart and breath signal processors and a temperature signal processor.

11. The system of claim 10 wherein said heart and breath sensors include patient engagable electrodes which are adapted for both heart and breath sensing.

12. The system of claim 10 wherein said sensing means also includes a blood pressure sensor, and wherein said plurality of signal processing means includes a systolic and diastolic blood pressure signal processor.

13. The system of claim 9 wherein said LCD display means is a four digital LCD display, and wherein said LCD driver means is a single hybrid circuit driving said four digit LCD display.

14. The system of claim 9 wherein said LCD driver means includes four drivers each of which is capable of driving a four digit LCD display, and wherein said LCD display means includes a plurality of LCDs sufficient to individually display each digit indicative of the vital signs sensed by said sensing means.

15. The system of claim 14 wherein said select means includes sixteen select lines, and wherein each of said lines is activated in turn so that each digit is displayed in turn at said LCD display.

16. The system of claim 9 wherein said plurality of sensing means includes an ECG amplifier and cardiotachometer signal conditioner unit and an impedance pneumograph and respiration rate signal conditioner unit, wherein said plurality of signal processing means includes a heart/breath rate processor unit, and wherein said system includes selector switch means for controlling the unit to be connected with said processor unit.

17. The system of claim 16 wherein said ECG amplifier and cardiotachometer signal conditioner unit includes a balanced differential amplifier and bandpass filter means.

18. The system of claim 16 wherein said ECG amplifier and cardiotachometer signal conditioner unit includes pulse forming circuitry with automatic gain control for assuring of forming of said pulse over a wide range of amplitute of input signal.

19. The system of claim 16 wherein said ECG amplifier and cardiotachometer signal conditioner unit includes a normalizing circuit that includes means for producing a predetermined maximum amplitude output signal regardless of polarity and bipolar threshold means for establishing a threshold below said predetermined maximum amplitude output signal.

20. The system of claim 16 wherein said pneumograph and respiration rate signal conditioner unit includes signal generating means for producing a signal for driving patient engagable electrodes when connected with the generating means so that said signal is amplitude modulated due to breathing of a patient in engagement with said electrodes, a balanced differential amplifier connectable with said patient engagable electrodes to receive said amplitude modulation signal therefrom, and rectifier means connected with said balanced differential amplifier for detecting amplitude modulation on said amplitude modulated signal.

21. The system of claim 20 wherein said pneumograph and respiration rate signal conditioner unit includes a second order low pass filter and a bipolar d.c. restorer for discriminating against unwanted signals.

22. The system of claim 20 wherein said pneumograph and respiration rate signal conditioner unit includes a threshold circuit with hystersis to form a squarewave output signal to be coupled from said unit.

23. The system of claim 16 wherein said selector switch means is also connected with said plurality of signal processing means whereby selection of the vital sign to be monitored is controlled by said selector switch means.

24. The system of claim 16 wherein said heart/breath rate processor unit includes digital components for producing said BCD output data.

25. The system of claim 24 wherein said digital components include a plurality of interconnected counters, switches and latch registers each of which is a CMOS device.

26. The system of claim 24 wherein said unit includes a first means for receiving pulses coupled thereto indicative of one of heart and breath signals, second means connected with said first means for determining one of heart and breath rate in BCD form, and output means connected with said second means for providing said BCD output data.

27. The system of claim 24 wherein said first means is an edge triggered counter for counting received pulses, wherein said second means includes a plurality of interconnected counters, switches and latch registers, and wherein said output means includes a tri-state output latch register having a four line output.

28. The system of claim 9 wherein said plurality of signal processing means includes a temperature processor unit connected with said temperature sensor.

29. The system of claim 28 wherein said temperature processor unit includes amplifying means, analog-to-digital converter means, and output means for providing a BCD output.

30. The system of claim 29 wherein said sensing means is a thermistor, wherein said amplifying means includes a first operational amplifier, wherein said unit includes means for linearizing said thermistor output with respect to indicated temperatures, and wherein said unit includes a Zener diode and a second operational amplifier for providing a reference voltage to said first operational amplifier.

31. The system of claim 29 wherein said output means includes a tri-state output latch register for providing a four line BCD digit output.

32. The system of claim 9 wherein said timing means includes a clock unit having a single frequency generating source for providing timing signals to said signal processing means and said LCD device.

33. The system of claim 32 wherein said clock unit includes a crystal controlled oscillator and a plurality of frequency dividers connected with said crystal controlled oscillator to produce said timing signals.

34. The system of claim 9 wherein said LCD driver means includes a plurality of BCD to LCD display decoders for receiving BCD data on data lines from said plurality of signal processing means, a counter for receiving an input from said timing means, and one of four decoder means connected with said BCD to LCD display decoders, said one of four decoder means also forming a part of said select means for selecting said BCD output data to be coupled to said LCD driver means.

35. The system of claim 34 wherein said plurality of BCD to LCD display decoder includes four decoders, wherein said counter is a ÷16 circuit, and wherein said one of four decoder means includes a pair of one of four decoders.

36. An integrated system having a plurality of hybrid circuits for monitoring vital physiological signs and displaying the same, said system comprising:

an ECG amplifier and cardiotachometer signal conditioner unit having a plurality of patient engageable electrodes for sensing heart signals, said unit including pulse forming circuitry suitable for forming said pulse for a wide range of amplitudes of input heart signals, and said unit providing output pulses indicative of sensed heart signals;

an impedance pneumograph and respiration signal conditioner unit having input means connected with said plurality of electrodes and including signal generating means for producing a drive signal connected with said input means to drive said electrodes connected therewith so that said drive signal is amplitude modulated due to breathing of a patient in engagement with said electrodes, said unit also including means connected with said input means to detect said amplitude modulation on said driven signal and developing therefrom pulses indicative of sensed breath signals;

selector means for selecting and passing pulse outputs from one of said ECG amplifier and cardiotachometer signal conditioner unit and said impedance pneumograph and respiration rate signal conditioner unit;

a rate processor for receiving said selected pulse output passed by said selector means, said rate processor including means responsive to said received pulses for generating BCD output data, and said rate processor including a tri-state latch register for providing a four line BCD digit output;

a temperature sensing element for sensing temperature and providing an output signal indicative thereof;

a temperature processor for receiving said output signal from said temperature sensing element, said temperature processor including analog-to-digital converting means for providing a digital outpt indicative of sensed temperature, means responsive to said digital output for generating BCD data, and a tri-state latch register for providing a four line BCD digit output;

an LCD driver having a four line input connected with each of said tri-state latch registors of said processors for receiving BCD output data therefrom, said LCD driver responsive to received BCD output data providing LCD drive signals, and said LCD driver also including means connected with said processors to select said BCD output data coupled to said LCD driver on said four lines;

timing means connected with said LCD driver and said processors for coupling timing signals thereto; and LCD display means connected with said LCD driver for receiving said LCD drive signals therefrom and responsive thereto providing a visual vital sign display.

37. A vital physiological sign monitoring and display system, comprising:

a temperature sensor for sensing temperature and providing an output indicative thereof;

a temperature processor for receiving said output from said temperature sensor and responsive thereto providing a four line BCD output;

an ECG amplifier having a plurality of electrodes engagable with a patient for sensing heart signals from a patient in engagement with said electrodes and providing an output indicative thereof;

a heart rate processor for receiving said output from said ECG amplifier and responsive thereto providing a four line BCD output;

an impedance pneumograph amplifier connectable with said plurality of electrodes for receiving breath signals therefrom and providing an output indicative thereof;

a breath rate processor for receiving said output from said impedance pneumograph amplifier and responsive thereto providing a four line BCD output;

a pressure and sound transducer for sensing blood pressure of a patient adjacent thereto and providing an output indicative thereof;

a systolic/diastolic blood pressure processor for receiving said output from said pressure and sound transducer and responsive thereto providing a four line BCD output;

coupling means consisting of four data lines connected with the four line BCD output of each of said processors;

four LCD display drivers connected with said coupling means to receive said BCD data therefrom and providing display drive output signals, each of said LCD display driver units providing a four line select output coupled to said processors for controlling BCD data flow from said processors to said LCD display drivers;

a frequency generator for providing timing signals to said processors and LCD display drivers; and a plurality of display LCDs connected with said LCD display drivers to receive said display drive output signals therefrom and responsive thereto for displaying temperature, heart rate, breath rate, systolic blood pressure, and diastolic blood pressure.

* * * * *